(12) United States Patent
Momo et al.

(10) Patent No.: US 11,848,429 B2
(45) Date of Patent: Dec. 19, 2023

(54) SEMICONDUCTOR DEVICE AND ELECTRONIC DEVICE

(71) Applicant: SEMICONDUCTOR ENERGY LABORATORY CO., LTD., Atsugi (JP)

(72) Inventors: Junpei Momo, Kanagawa (JP); Kazutaka Kuriki, Kanagawa (JP); Hiromichi Godo, Kanagawa (JP); Shunpei Yamazaki, Tokyo (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 17/676,874

(22) Filed: Feb. 22, 2022

(65) Prior Publication Data

US 2022/0181711 A1 Jun. 9, 2022

Related U.S. Application Data

(63) Continuation of application No. 17/019,700, filed on Sep. 14, 2020, now Pat. No. 11,342,599, which is a continuation of application No. 16/360,065, filed on Mar. 21, 2019, now Pat. No. 10,862,177, which is a continuation of application No. 15/117,349, filed as application No. PCT/IB2015/050768 on Feb. 2, 2015, now Pat. No. 10,290,908.

(30) Foreign Application Priority Data

Feb. 14, 2014 (JP) .................................. 2014-026312

(51) Int. Cl.
*H01M 10/46* (2006.01)
*H02J 50/20* (2016.01)
(Continued)

(52) U.S. Cl.
CPC ............ *H01M 10/46* (2013.01); *A61N 1/378* (2013.01); *G06F 1/163* (2013.01);
(Continued)

(58) Field of Classification Search
CPC .. H01M 10/46; H01M 10/613; H01M 10/623; H01M 10/052; H01M 10/0525;
(Continued)

(56) References Cited

U.S. PATENT DOCUMENTS

| 5,375,226 A | 12/1994 | Sano et al. |
| 5,890,780 A | 4/1999 | Tomiyori |

(Continued)

FOREIGN PATENT DOCUMENTS

| CN | 001754260 A | 3/2006 |
| CN | 101454788 A | 6/2009 |

(Continued)

OTHER PUBLICATIONS

International Search Report (Application No. PCT/IB2015/050768) dated May 19, 2015.
(Continued)

*Primary Examiner* — Jane J Rhee
(74) *Attorney, Agent, or Firm* — NIXON PEABODY LLP; Jeffrey L. Costellia

(57) ABSTRACT

A semiconductor device in which a circuit and a battery are efficiently stored is provided. In the semiconductor device, a first transistor, a second transistor, and a secondary battery are provided over one substrate. A channel region of the second transistor includes an oxide semiconductor. The secondary battery includes a solid electrolyte, and can be fabricated by a semiconductor manufacturing process. The substrate may be a semiconductor substrate or a flexible substrate. The secondary battery has a function of being wirelessly charged.

7 Claims, 16 Drawing Sheets

(51) Int. Cl.
  *H01M 10/0562* (2010.01)
  *H01M 10/613* (2014.01)
  *H01L 21/822* (2006.01)
  *H01L 27/06* (2006.01)
  *H01M 10/052* (2010.01)
  *H01M 10/42* (2006.01)
  *H01M 10/623* (2014.01)
  *A61N 1/378* (2006.01)
  *G06F 1/16* (2006.01)
  *H01L 27/12* (2006.01)
  *H01L 29/786* (2006.01)
  *H01M 10/0525* (2010.01)
  *H01M 10/0585* (2010.01)

(52) U.S. Cl.
  CPC ...... *H01L 21/8221* (2013.01); *H01L 27/0688* (2013.01); *H01L 27/124* (2013.01); *H01L 27/1218* (2013.01); *H01L 27/1225* (2013.01); *H01L 27/1251* (2013.01); *H01L 29/7869* (2013.01); *H01L 29/78651* (2013.01); *H01M 10/052* (2013.01); *H01M 10/0525* (2013.01); *H01M 10/0562* (2013.01); *H01M 10/0585* (2013.01); *H01M 10/425* (2013.01); *H01M 10/613* (2015.04); *H01M 10/623* (2015.04); *H02J 50/20* (2016.02); *H01M 2220/30* (2013.01); *H01M 2300/0071* (2013.01)

(58) Field of Classification Search
  CPC ......... H01M 10/0562; H01M 10/0585; H01M 10/425; H01M 2220/30; H01M 2300/0071
  See application file for complete search history.

(56) References Cited

U.S. PATENT DOCUMENTS

| | | | |
|---|---|---|---|
| 6,264,709 | B1 | 7/2001 | Yoon et al. |
| 7,253,494 | B2 | 8/2007 | Mino et al. |
| 7,723,804 | B2 | 5/2010 | Ajiki |
| 7,777,468 | B2 | 8/2010 | Okuda et al. |
| 7,952,328 | B2* | 5/2011 | Parker .................... G06F 1/263 320/112 |
| 8,378,403 | B2 | 2/2013 | Kato |
| 8,400,278 | B2 | 3/2013 | Koyama |
| 8,415,731 | B2 | 4/2013 | Yamazaki et al. |
| 8,463,332 | B2 | 6/2013 | Sato et al. |
| 8,810,375 | B2 | 8/2014 | Koyama |
| 8,984,310 | B2 | 3/2015 | Kuroishi et al. |
| 9,006,024 | B2 | 4/2015 | Akimoto |
| 9,059,219 | B2 | 6/2015 | Sasagawa et al. |
| 9,172,237 | B2 | 10/2015 | Sato |
| 9,219,164 | B2 | 12/2015 | Yamazaki |
| 9,276,121 | B2 | 3/2016 | Yamazaki |
| 9,299,723 | B2 | 3/2016 | Saito |
| 9,312,390 | B2 | 4/2016 | Yamazaki |
| 9,384,439 | B2 | 7/2016 | Yamazaki et al. |
| 9,472,682 | B2 | 10/2016 | Yamazaki et al. |
| 9,477,249 | B2 | 10/2016 | Takahashi et al. |
| 9,536,422 | B2 | 1/2017 | Yamazaki |
| 9,640,639 | B2 | 5/2017 | Yamazaki |
| 9,831,704 | B2 | 11/2017 | Uramoto et al. |
| 9,887,568 | B2 | 2/2018 | Yamazaki et al. |
| 9,922,551 | B2 | 3/2018 | Yamazaki |
| 9,998,003 | B2 | 6/2018 | Takahashi et al. |
| 10,097,052 | B2 | 10/2018 | Uramoto et al. |
| 2006/0113652 | A1 | 6/2006 | Mino et al. |
| 2007/0285246 | A1 | 12/2007 | Koyama |
| 2008/0058029 | A1 | 3/2008 | Sato et al. |
| 2008/0158217 | A1 | 7/2008 | Hata et al. |
| 2009/0058361 | A1 | 3/2009 | John |
| 2010/0304550 | A1 | 12/2010 | Moriwaka |
| 2011/0101913 | A1 | 5/2011 | Matsumoto et al. |
| 2012/0261998 | A1 | 10/2012 | Sato |
| 2012/0293893 | A1 | 11/2012 | Sato |
| 2013/0140554 | A1* | 6/2013 | Yamazaki ......... H01L 29/66742 257/43 |
| 2013/0191673 | A1 | 7/2013 | Koyama et al. |
| 2013/0265010 | A1 | 10/2013 | Nomura et al. |
| 2014/0004656 | A1 | 1/2014 | Sasagawa et al. |
| 2014/0009270 | A1 | 1/2014 | Yamazaki |
| 2014/0173300 | A1* | 6/2014 | Yamazaki ............. H02J 7/0031 713/300 |
| 2014/0368486 | A1 | 12/2014 | Hata et al. |
| 2017/0033205 | A1 | 2/2017 | Yamazaki et al. |
| 2018/0138729 | A1 | 5/2018 | Yamazaki et al. |

FOREIGN PATENT DOCUMENTS

| | | |
|---|---|---|
| EP | 1632999 A | 3/2006 |
| EP | 1939842 A | 7/2008 |
| EP | 2442430 A | 4/2012 |
| EP | 2512001 A | 10/2012 |
| JP | 59-032023 A | 2/1984 |
| JP | 02-178818 A | 7/1990 |
| JP | 10-112939 A | 4/1998 |
| JP | 2000-106366 A | 4/2000 |
| JP | 2002-049444 A | 2/2002 |
| JP | 2003-133420 A | 5/2003 |
| JP | 2004-045913 A | 2/2004 |
| JP | 2004-281593 A | 10/2004 |
| JP | 2004-320011 A | 11/2004 |
| JP | 2005-109616 A | 4/2005 |
| JP | 2006-032927 A | 2/2006 |
| JP | 2007-053265 A | 3/2007 |
| JP | 2008-009972 A | 1/2008 |
| JP | 2008-011597 A | 1/2008 |
| JP | 2008-172905 A | 7/2008 |
| JP | 2008-181108 A | 8/2008 |
| JP | 2009-003874 A | 1/2009 |
| JP | 2011-010501 A | 1/2011 |
| JP | 2011-101458 A | 5/2011 |
| JP | 2011-188733 A | 9/2011 |
| JP | 2012-090373 A | 5/2012 |
| JP | 2012-223070 A | 11/2012 |
| JP | 2012-256941 A | 12/2012 |
| JP | 2012-257447 A | 12/2012 |
| JP | 2013-084083 A | 5/2013 |
| JP | 2013-125782 A | 6/2013 |
| JP | 2013-153640 A | 8/2013 |
| JP | 2013-172379 A | 9/2013 |
| JP | 2013-226039 A | 10/2013 |
| JP | 2013-233072 A | 11/2013 |
| JP | 2013-236068 A | 11/2013 |
| JP | 2013-243349 A | 12/2013 |
| JP | 2013-251884 A | 12/2013 |
| JP | 2013-254942 A | 12/2013 |
| JP | 2014-003280 A | 1/2014 |
| JP | 2014-029994 A | 2/2014 |
| JP | 2014-030000 A | 2/2014 |
| JP | 2014-030192 A | 2/2014 |
| KR | 2009-0024754 A | 3/2009 |
| KR | 2014-0001117 A | 1/2014 |
| WO | WO-2004/090982 | 10/2004 |
| WO | WO-2007/139205 | 12/2007 |
| WO | WO-2011/145468 | 11/2011 |

OTHER PUBLICATIONS

Written Opinion (Application No. PCT/IB2015/050768) dated May 19, 2015.

* cited by examiner

SEMICONDUCTOR DEVICE AND ELECTRONIC DEVICE

TECHNICAL FIELD

The present invention relates to an object, a method, or a manufacturing method. In addition, the present invention relates to a process, a machine, manufacture, or a composition of matter. One embodiment of the present invention relates to a semiconductor device, a display device, a light-emitting device, a power storage device, a memory device, a driving method thereof, or a manufacturing method thereof. In particular, one embodiment of the present invention relates to a semiconductor device, a display device, or a light-emitting device each including an oxide semiconductor.

In this specification and the like, a semiconductor device generally means a device that can function by utilizing semiconductor characteristics. A display device, an electro-optical device, a semiconductor circuit, and an electronic device include a semiconductor device in some cases.

BACKGROUND ART

Electronic devices carried around by the users and electronic devices worn by the users have been actively developed.

Since electronic devices carried around by the users and electronic devices worn by the users are powered by batteries, their power consumption is reduced as much as possible. Particularly in the case where a central processing unit (CPU), which consumes a lot of power for its operation, is included in the electronic device, processing of the CPU greatly affects the power consumption of the electronic device.

A semiconductor device including a high-performance integrated circuit (e.g., a CPU) over a plastic or plastic film substrate, which transmits and receives electric power or signals wirelessly, is described in Patent Document 1.

A semiconductor device in which a register in a CPU is formed using a memory circuit including an oxide semiconductor transistor to reduce power consumption is described in Patent Document 2.

Furthermore, a technique for fabricating a semiconductor element and an all-solid-state battery that includes a solid electrolyte over a semiconductor substrate, for miniaturizing an electronic device, has been proposed in recent years (Patent Document 3).

REFERENCE

Patent Document

[Patent Document 1] Japanese Published Patent Application No. 2006-32927
[Patent Document 2] Japanese Published Patent Application No. 2013-251884
[Patent Document 3] Japanese Published Patent Application No. 2003-133420

DISCLOSURE OF INVENTION

The details of the power consumption of an electronic device including a CPU will be described. The power consumption can be roughly classified into power consumed by a CPU, power consumed by systems around the CPU, and power consumed by a plurality of input/output devices and peripheral devices connected to the inside or outside of the electronic device. The power consumed by systems around the CPU includes a loss in a converter, a loss in a wiring pattern, and power consumed by a bus, a controller, and the like.

When an electronic device is reduced in size or thickness, a battery is also subjected to the limitation. As for a battery, however, decrease in volume leads to decrease in capacity. Thus, a circuit, a battery, and the like are stored in a smaller space.

Furthermore, a battery generates heat by charge and discharge, which may thermally affect the surrounding area.

As an electronic device is reduced in size and a circuit, a battery, and the like are stored in a smaller space, how to control the power consumption and heat generation becomes a problem.

One embodiment of the present invention provides a novel semiconductor device, a semiconductor device in which a circuit and a battery are efficiently stored, a semiconductor with small power consumption, or a semiconductor device with reduced heat generation.

Furthermore, one embodiment of the present invention provides an electronic device having a novel structure, specifically, an electronic device having a novel structure that can be changed in form in various ways. More specifically, a wearable electronic device that is used while being worn on the body and an electronic device that is used while being implanted in the body are provided.

Note that the description of a plurality of objects does not mutually preclude the existence. Note that one embodiment of the present invention does not necessarily achieve all the objects listed above. Objects other than those listed above are apparent from the description of the specification, drawings, and claims, and also such objects could be an object of one embodiment of the present invention.

One embodiment of the present invention is a semiconductor device including a first transistor, a second transistor, and a secondary battery. The first transistor, the second transistor, and the secondary battery are provided over a substrate. A channel region of the first transistor includes silicon. A channel region of the second transistor includes an oxide semiconductor. The secondary battery includes a solid electrolyte.

In the above embodiment, the substrate is preferably flexible.

In the above embodiment, the secondary battery preferably has a function of being wirelessly charged.

In the above embodiment, the secondary battery preferably includes lithium. In addition, an insulating film including halogen may be provided between the secondary battery and the first transistor or between the secondary battery and the second transistor.

In the above embodiment, a cooling device may be provided over the secondary battery.

In the above embodiment, the secondary battery is preferably fabricated by a semiconductor manufacturing process.

One embodiment of the present invention is an electronic device including a display device and the semiconductor device according to the above embodiment.

According to one embodiment of the present invention, it becomes possible to provide a novel semiconductor device, a semiconductor device in which a circuit and a battery are efficiently stored, a semiconductor device with small power consumption, or a semiconductor device with reduced heat generation.

Furthermore, according to one embodiment of the present invention, it becomes possible to provide an electronic device with a novel structure. Specifically, it becomes possible to provide an electronic device having a novel structure that can be changed in form in various ways. More specifically, it becomes possible to provide a wearable electronic device that is used while being worn on the body and an electronic device that is used while being implanted in the body.

Note that the description of these effects does not disturb the existence of other effects. One embodiment of the present invention does not necessarily achieve all the effects listed above. Other effects will be apparent from and can be derived from the description of the specification, the drawings, the claims, and the like.

BEST MODE FOR CARRYING OUT THE INVENTION

Figure 1:
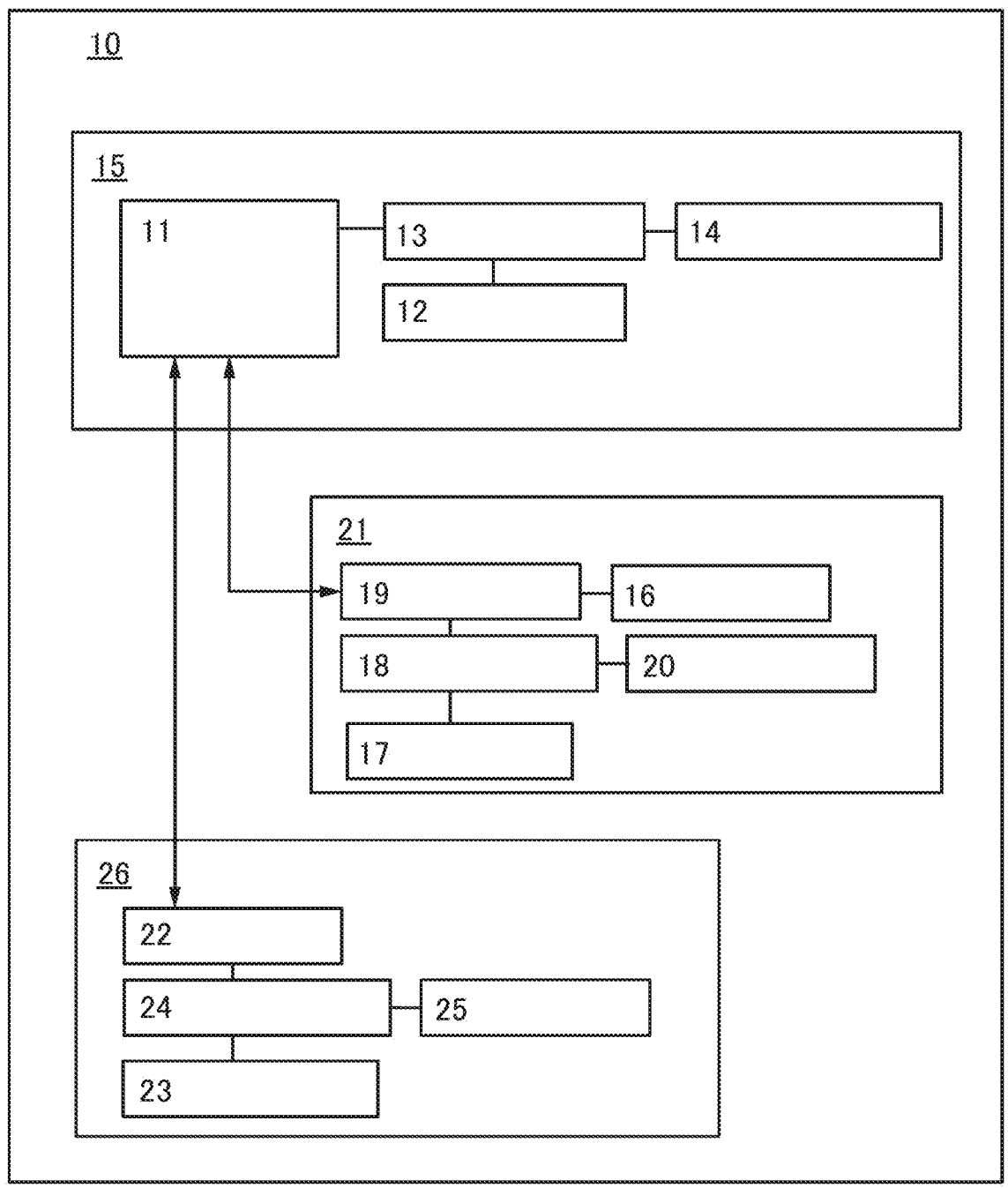
FIG. 1 is a block diagram illustrating one embodiment of the present invention.

Hereinafter, embodiments will be described with reference to drawings. However, the embodiments can be implemented with various modes. It will be readily appreciated by those skilled in the art that modes and details can be changed in various ways without departing from the spirit and scope of the present invention. Thus, the present invention should not be interpreted as being limited to the following description of the embodiments. In addition, in the following embodiments and examples, the same portions or portions having similar functions are denoted by the same reference numerals in different drawings, and description thereof will not be repeated.

In the drawings, the size, the layer thickness, or the region is exaggerated for clarity in some cases. Therefore, embodiments of the present invention are not limited to such a scale. Note that the drawings are schematic views showing ideal examples, and embodiments of the present invention are not limited to shapes or values shown in the drawings.

Note that in this specification, ordinal numbers such as "first", "second", and "third" are used in order to avoid confusion among components, and the terms do not limit the components numerically.

Note that in this specification, terms for describing arrangement, such as "over" "above", "under", and "below", are used for convenience in describing a positional relation between components with reference to drawings. Furthermore, the positional relation between components is changed as appropriate in accordance with a direction in which each component is described. Thus, the positional relation can be described in different ways as appropriate depending on the situation, without being limited to the term used in this specification.

In this specification and the like, a transistor is an element having at least three terminals of a gate, a drain, and a source. In addition, the transistor has a channel region between a drain (a drain terminal, a drain region, or a drain electrode layer) and a source (a source terminal, a source region, or a source electrode layer), and current can flow through the drain, the channel region, and the source. Note that in this specification and the like, a channel region refers to a region through which current mainly flows.

Furthermore, functions of a source and a drain might be switched when transistors having different polarities are employed or a direction of current flow is changed in circuit operation, for example. Therefore, the terms "source" and "drain" can be switched in this specification and the like.

Note that in this specification and the like, the expression "electrically connected" includes the case where components are connected through an "object having any electric function". There is no particular limitation on an "object having any electric function" as long as electric signals can be transmitted and received between components that are connected through the object. Examples of an "object having any electric function" are a switching element such as a transistor, a resistor, an inductor, a capacitor, and elements with a variety of functions as well as an electrode and a wiring.

Embodiment 1

<Block Diagram of Device>

FIG. 1 is a block diagram of a device 10 that is one embodiment of the present invention.

The device 10 of this embodiment includes a control module 15, a display module 21, and a communication module 26. The control module 15 is a controller that controls the entire device 10, communication, and display of information on a display portion 16.

The control module 15 includes a CPU 11, a battery 12, a regulator 13, and a wireless receiving portion 14.

The display module 21 includes the display portion 16, a display driver circuit 19, a battery 17, a regulator 18, and a wireless receiving portion 20.

The communication module 26 includes a communication circuit 22, a battery 23, a regulator 24, and a wireless receiving portion 25.

A regulator is an electronic circuit that keeps an output voltage or current constant. A regulator is classified into two kinds, a linear regulator and a switching regulator, depending on the amount of electric load or the like. A switching regulator is also called a DC-DC converter.

Each module includes a regulator and a battery. Each battery is a secondary battery, which can be charged and discharged repeatedly, and is connected to a circuit in order that it can be wirelessly charged. The batteries are electrically connected to the respective wireless receiving portions via the respective regulators. Each regulator supplies necessary electric power or signals to the functional circuit, from the connected battery. In addition, each regulator also has a function of preventing overcharge and the like when the connected battery is charged.

In the device 10, each of the modules can be turned on or turned off independently. The operation system that selectively drives only the module to be used can reduce power consumption of the device 10.

For example, when the user looks at information on the display portion 16 without using a communication function, the communication circuit 22 is in an off state where the battery 23 is not used in order that electric power to the communication circuit 22 is blocked in the communication module 26, while the display module 21 and the control module 15 are in an on state.

Furthermore, for a still image, once the still image is displayed on the display portion 16 with the display module 21 and the control module 15 being in an on state, the still image can be kept displayed while only the display module 21 is in an on state even after the control module 15 is turned off with the still image being displayed. In that case, the control module 15 is not operated although the still image is displayed, and the power consumed by the control module 15 can apparently be zero. Note that when transistors of the display portion 16 use an oxide semiconductor layer with low off-state current (e.g., an oxide material including In, Ga, and Zn), or when the display portion 16 includes a memory for each of the pixels, the still image can be kept displayed for a certain period even when the supply of electric power from the battery 17 is blocked after the still image is displayed.

In this manner, a battery is provided for each of the components to be used in the electronic device, and only the component in use is selectively driven, whereby the power consumption can be reduced.

Note that a memory cell including an oxide semiconductor transistor is preferably used for a register in the CPU 11. With the use of an oxide semiconductor transistor in the CPU 11, even in the case where the operation of the CPU 11 is temporarily stopped and the supply of the power supply voltage is stopped, data can be held and power consumption can be reduced. Specifically, for example, while a user of a personal computer does not input data to an input device such as a keyboard, the operation of the CPU 11 can be stopped, whereby the power consumption can be reduced.

Furthermore, the use of oxide semiconductor transistors as the transistors used for the regulators 13, 18, and 24 can reduce power consumption because of the small off-state current. In particular, a regulator (DC-DC converter) including a control circuit including oxide semiconductor transistors can operate at a temperature of 150° C. or higher. Thus, such a DC-DC converter is preferably used for an electronic device that is likely to operate at high temperatures.

In this embodiment, an example in which the display module 21, the control module 15, and the communication module 26 each have a battery is described; however, the total number of batteries is not limited to three. The electronic device may additionally include functional modules and their batteries, in which case the electronic device has four or more batteries in total.

For example, if an exterior body of the device 10 is formed of a flexible material, a wearable device that is used while being worn on the body can be provided. In that case, if small-sized batteries are dispersedly arranged in the device 10, a feeling of weight can be reduced as compared to an electronic device having a single large battery. In addition, even if the individual small-sized battery generates heat, it does not ruin the comfort of wearing the device.

Next, a semiconductor device that can be used for the device 10 will be described with reference to FIGS. 2 to 4.

Structural Example 1 of Semiconductor Device

Figure 2:
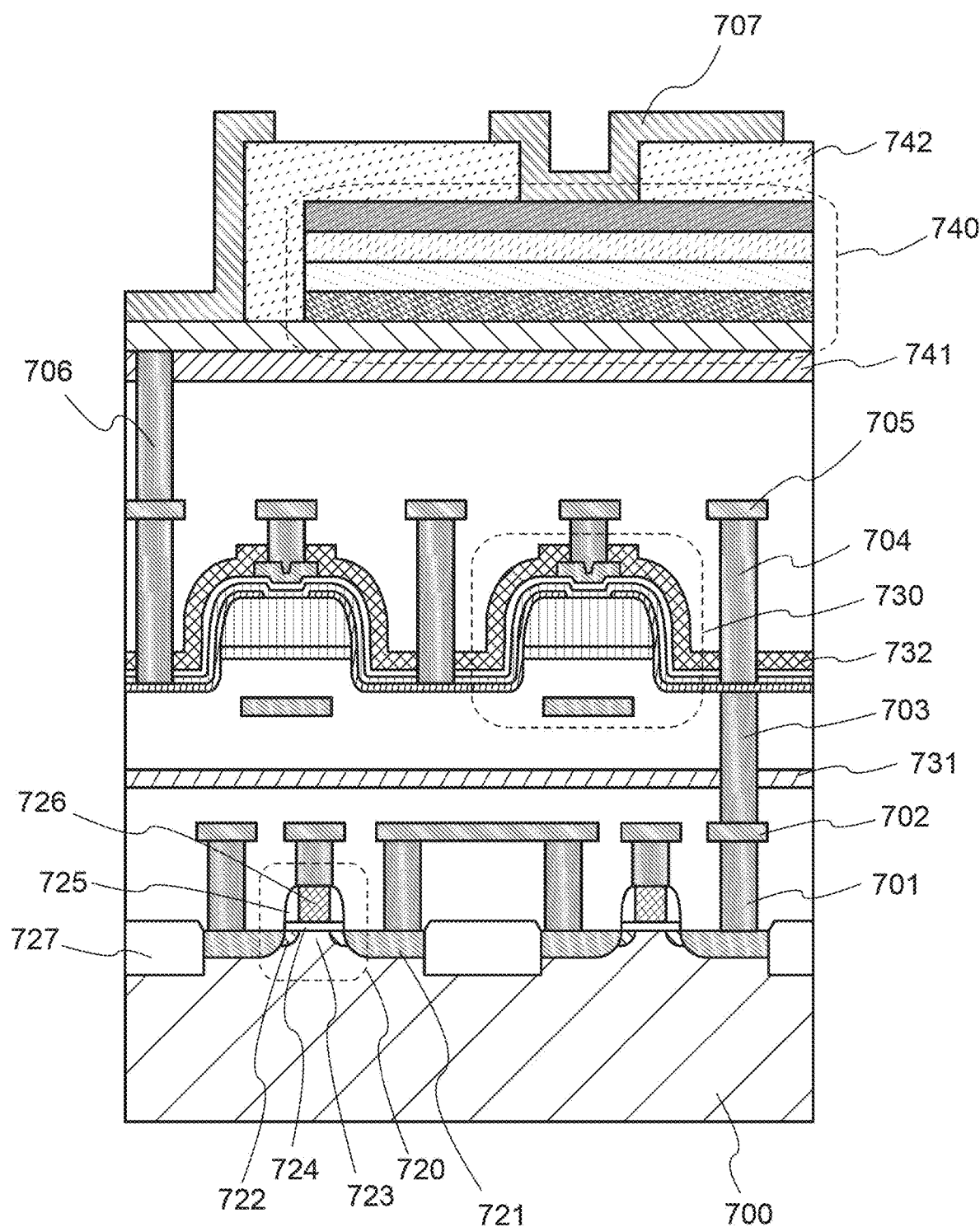
FIG. 2 is a cross-sectional view of a semiconductor device of one embodiment of the present invention.

FIG. 2 shows a cross-sectional view of a semiconductor device 1000 including a transistor 720, a transistor 730, and a battery 740 that are formed over the same substrate. The transistor 720 is provided over a substrate 700, the transistor 730 is provided over the transistor 720, and the battery 740 is provided over the transistor 730.

The semiconductor device 1000 includes the substrate 700, the transistor 720, an element isolation layer 727, an insulating film 731, the transistor 730, an insulating film 732, an insulating film 741, the battery 740, an insulating film 742, plugs 701, 703, 704, and 706, and wirings 702, 705, and 707. The transistor 720 includes a gate electrode 726, a gate insulating film 724, a sidewall insulating layer 725, an impurity region 721 functioning as a source region or a drain region, an impurity region 722 functioning as a lightly doped drain (LDD) region or an extension region, and a channel region 723.

The impurity concentration is higher in the impurity region 721 than in the impurity region 722. The impurity region 721 and the impurity region 722 can be formed in a self-aligned manner, with the gate electrode 726 and the sidewall insulating layer 725 used as a mask.

As the substrate 700, a single crystal semiconductor substrate or a polycrystalline semiconductor substrate of silicon or silicon carbide, a compound semiconductor substrate of silicon germanium, a silicon-on-insulator (SOI) substrate, or the like may be used. A transistor manufactured using a semiconductor substrate can operate at high speed easily. In the where a p-type single crystal silicon substrate is used as the substrate 700, an impurity element imparting n-type conductivity may be added to part of the substrate 700 to form an n-well, and a p-type transistor can be formed in a region where the n-well is formed. As the impurity element imparting n-type conductivity, phosphorus (P), arsenic (As), or the like can be used. As the impurity element imparting p-type conductivity, boron (B) or the like may be used.

Alternatively, the substrate 700 may be an insulating substrate over which a semiconductor film is provided. Examples of the insulating substrate include a glass substrate, a quartz substrate, a plastic substrate, a metal substrate, a stainless steel substrate, a substrate including stainless steel foil, a tungsten substrate, a substrate including tungsten foil, a flexible substrate, an attachment film, paper including a fibrous material, and a base film. As an example of a glass substrate, a barium borosilicate glass substrate, an aluminoborosilicate glass substrate, a soda lime glass substrate, or the like can be given. Examples of a flexible substrate include a flexible synthetic resin such as plastics typified by polyethylene terephthalate (PET), polyethylene naphthalate (PEN), and polyether sulfone (PES), and acrylic. Examples of an attachment film are attachment films formed using polypropylene, polyester, polyvinyl fluoride, polyvinyl chloride, and the like. Examples of a base film are base films formed using polyester, polyimide, polyimide, aramid, epoxy, an inorganic vapor deposition film, and paper.

Alternatively, a semiconductor element may be formed using one substrate, and then, transferred to another substrate. Examples of a substrate to which a semiconductor element is transferred include, in addition to the above-described substrates, a paper substrate, a cellophane substrate, an aramid film substrate, a polyimide film substrate, a stone substrate, a wood substrate, a cloth substrate (including a natural fiber (e.g., silk, cotton, or hemp), a synthetic fiber (e.g., nylon, polyurethane, or polyester), a regenerated fiber (e.g., acetate, cupra, rayon, or regenerated polyester, or the like), a leather substrate, and a rubber substrate. When such a substrate is used, a transistor with excellent properties or a transistor with low power consumption can be formed, a device with high durability, or high heat resistance can be provided, or reduction in weight or thickness can be achieved.

The transistor 720 is separated from other transistors formed on the substrate 700 by an element isolation layer 727.

As the transistor 720, a transistor containing silicide (salicide) or a transistor which does not include a sidewall insulating layer may be used. When a structure that contains silicide (salicide) is used, resistance of the source region and the drain region can be further lowered and the speed of the semiconductor device can be increased. Furthermore, the semiconductor device can be operated at low voltage; thus, power consumption of the semiconductor device can be reduced.

When a first semiconductor material is used for the transistor 720 and a second semiconductor material is used for the transistor 730, the first semiconductor material and the second semiconductor material are preferably materials having different band gaps. For example, the first semiconductor material can be a semiconductor material other than an oxide semiconductor (examples of such a semiconductor material include silicon (including strained silicon), germanium, silicon germanium, silicon carbide, gallium arsenide, aluminum gallium arsenide, indium phosphide, gallium nitride, and an organic semiconductor), and the second semiconductor material can be an oxide semiconductor. A transistor using a material other than an oxide semiconductor, such as single crystal silicon, can operate at high speed easily. In contrast, a transistor including an oxide semiconductor has a low off-state current.

The details of the oxide semiconductor transistor will be described later in Embodiment 3.

Here, in the case where a silicon-based semiconductor material is used for the transistor 720 provided in a lower portion, hydrogen in an insulating film provided in the vicinity of the semiconductor film of the transistor 720 terminates dangling bonds of silicon; accordingly, the reliability of the transistor 720 can be improved. Meanwhile, in the case where an oxide semiconductor is used for the transistor 730 provided in an upper portion, hydrogen in an insulating film provided in the vicinity of the semiconductor film of the transistor 730 becomes a factor of generating carriers in the oxide semiconductor; thus, the reliability of the transistor 730 might be decreased. Therefore, in the case where the transistor 730 using an oxide semiconductor is provided over the transistor 720 using a silicon-based semiconductor material, it is particularly effective that the insulating film 731 having a function of preventing diffusion of hydrogen is provided between the transistors 720 and 730. The insulating film 731 makes hydrogen remain in the lower portion, thereby improving the reliability of the transistor 720. In addition, since the insulating film 731 suppresses diffusion of hydrogen from the lower portion to the upper portion, the reliability of the transistor 730 can also be improved.

The insulating film 731 can be, for example, formed using aluminum oxide, aluminum oxynitride, gallium oxide, gallium oxynitride, yttrium oxide, yttrium oxynitride, hafnium oxide, hafnium oxynitride, or yttria-stabilized zirconia (YSZ).

Furthermore, the insulating film 732 having a function of preventing diffusion of hydrogen is preferably formed over the transistor 730 to cover the transistor 730 including an oxide semiconductor film. For the insulating film 732, a material that is similar to that of the insulating film 731 can be used, and in particular, an aluminum oxide film is preferably used. An aluminum oxide film has a high shielding (blocking) effect of preventing penetration of both oxygen and impurities such as hydrogen and moisture. Thus, by using an aluminum oxide film as the insulating film 732 covering the transistor 730, release of oxygen from the oxide semiconductor film included in the transistor 730 can be prevented and entry of water and hydrogen into the oxide semiconductor film can be prevented.

The plugs 701, 703, 704, and 706 and the wirings 702, 705, and 707 preferably have a single-layer structure or a stacked-layer structure of a conductive film containing a low-resistance material selected from copper (Cu), tungsten (W), molybdenum (Mo), gold (Au), aluminum (Al), manganese (Mn), titanium (Ti), tantalum (Ta), nickel (Ni), chromium (Cr), lead (Pb), tin (Sn), iron (Fe), and cobalt (Co), an alloy of such a low-resistance material, or a compound containing such a material as its main component. It is particularly preferable that the plugs and the wirings be formed using a Cu—Mn alloy, in which case manganese oxide formed at the interface with an insulator containing oxygen has a function of preventing Cu diffusion.

The battery 740 is a secondary battery, which can be charged and discharged repeatedly, and an all-solid-state battery including a solid electrolyte. Furthermore, in order to enable wireless charging, the battery 740 is electrically connected to a wireless receiving portion via a regulator.

In addition, the battery 740 can be fabricated with the use of a semiconductor manufacturing process. Note that the semiconductor manufacturing process refers to methods in general that are used for manufacturing semiconductor devices, such as a film formation process, a crystallization process, a plating process, a cleaning process, a lithography process, an etching process, a polishing process, an impurity implantation process, or a heat treatment process.

The details of the battery 740 will be described later in Embodiment 2.

The insulating film 741 can be formed to have a single-layer structure or a stacked-layer structure using one or more of silicon oxide, silicon oxynitride, silicon nitride oxide, silicon nitride, aluminum oxide, aluminum nitride, aluminum oxynitride, hafnium oxide, zirconium oxide, yttrium oxide, gallium oxide, lanthanum oxide, cesium oxide, tantalum oxide, and magnesium oxide.

In the case where the battery 740 includes lithium, the insulating film 741 preferably has a function of preventing (blocking) diffusion of lithium. When lithium that is included in the battery 740 enters a semiconductor element (the transistor 720 or the transistor 730) as a movable ion, the semiconductor element deteriorates. With the insulating film 741 blocking lithium ions, a highly reliable semiconductor device can be provided.

In the case where the battery 740 includes lithium, the insulating film 741 preferably includes halogen such as fluorine, chlorine, bromine, or iodine. When the insulating film 741 includes halogen, the halogen is easily combined with lithium that is an alkali metal. Then, lithium is fixed in the insulating film 741, whereby diffusion of lithium to the outside of the insulating film 741 can be prevented.

In the case where the insulating film 741 is formed of silicon nitride by a chemical vapor deposition (CVD) method, for example, when a halogen-containing gas is mixed in a source gas at 3% to 6% (volume ratio), e.g., at 5%, the obtained silicon nitride film includes the halogen. The concentration of the halogen element included in the insulating film 741, measured by secondary ion mass spectrometry (SIMS), is greater than or equal to $1 \times 10^{17}$ atoms/cm$^3$, preferably greater than or equal to $1 \times 10^{18}$ atoms/cm$^3$, and more preferably greater than or equal to $1 \times 10^{19}$ atoms/cm$^3$.

The insulating film 742 has a function of protecting the battery 740. As the insulating film 742, for example, an insulating material such as a resin (e.g., a polyimide resin, a polyamide resin, an acrylic resin, a siloxane resin, an epoxy resin, or a phenol resin), glass, an amorphous compound, or ceramics can be used. Furthermore, a layer containing calcium fluoride or the like may be provided as a water absorption layer between resin layers. The insulating film 742 can be formed by a spin coating method, an ink-jet method, or the like. Alternatively, the insulating film 742 can be formed to have a single-layer structure or a layered structure using one or more of silicon oxide, silicon oxynitride, silicon nitride oxide, silicon nitride, aluminum oxide, aluminum nitride, aluminum oxynitride, hafnium oxide, zirconium oxide, yttrium oxide, lanthanum oxide, gallium oxide, lanthanum oxide, cesium oxide, tantalum oxide, and magnesium oxide.

The semiconductor device 1000 may further include a semiconductor element over the battery 740. In that case, the insulating film 742 preferably has a function of preventing (blocking) diffusion of lithium, as with the insulating film 741. With the insulating film 742 blocking lithium, a highly reliable semiconductor device can be provided.

In the case where a semiconductor element is formed over the battery 740, the insulating film 742 preferably includes halogen such as fluorine, chlorine, bromine, or iodine, as with the insulating film 741. With the insulating film 742 including halogen, the halogen is easily combined with lithium that is an alkali metal, whereby diffusion of lithium to the outside of the insulating film 742 can be prevented.

Figure 3:
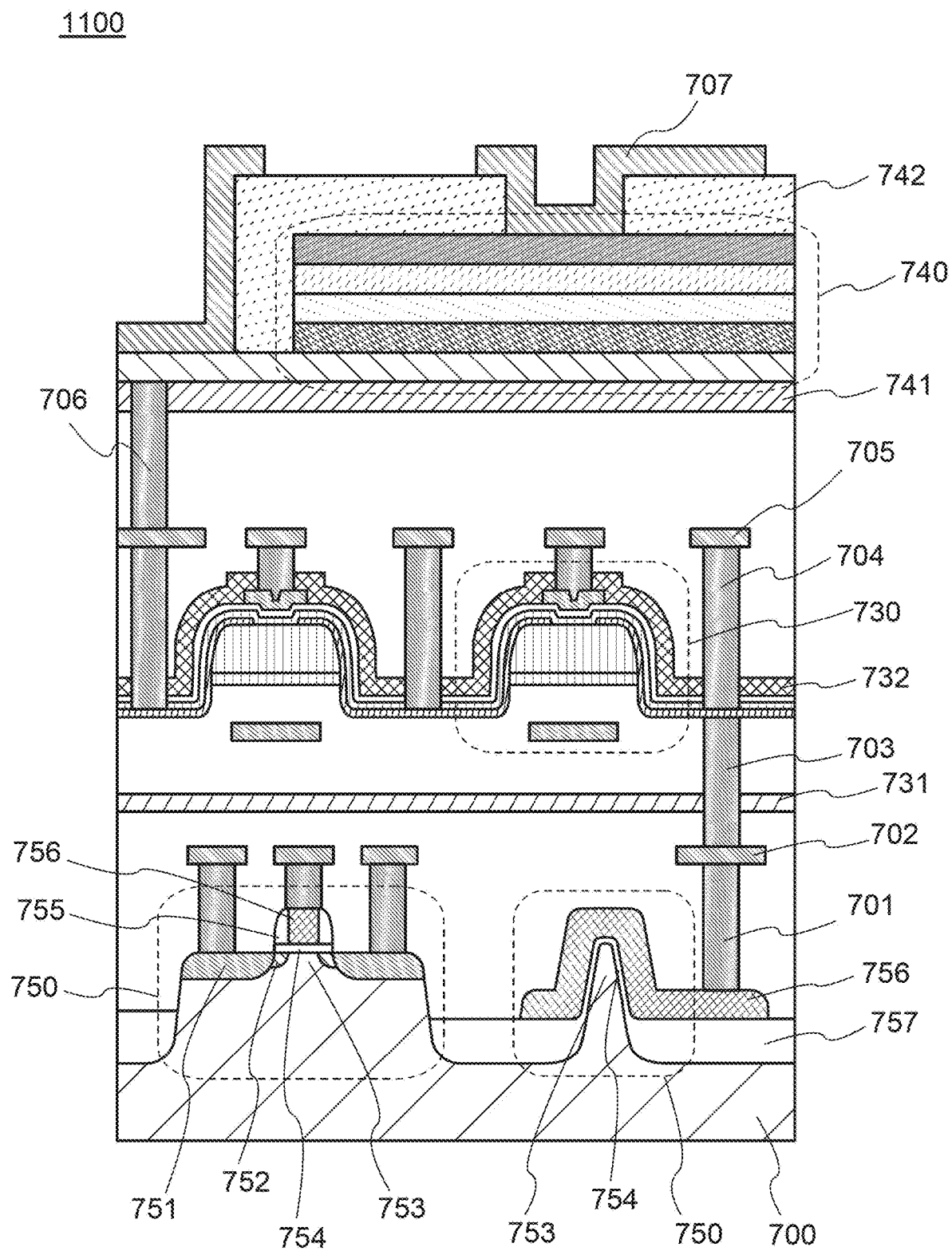
FIG. 3 is a cross-sectional view of a semiconductor device of one embodiment of the present invention.
Figure 4:
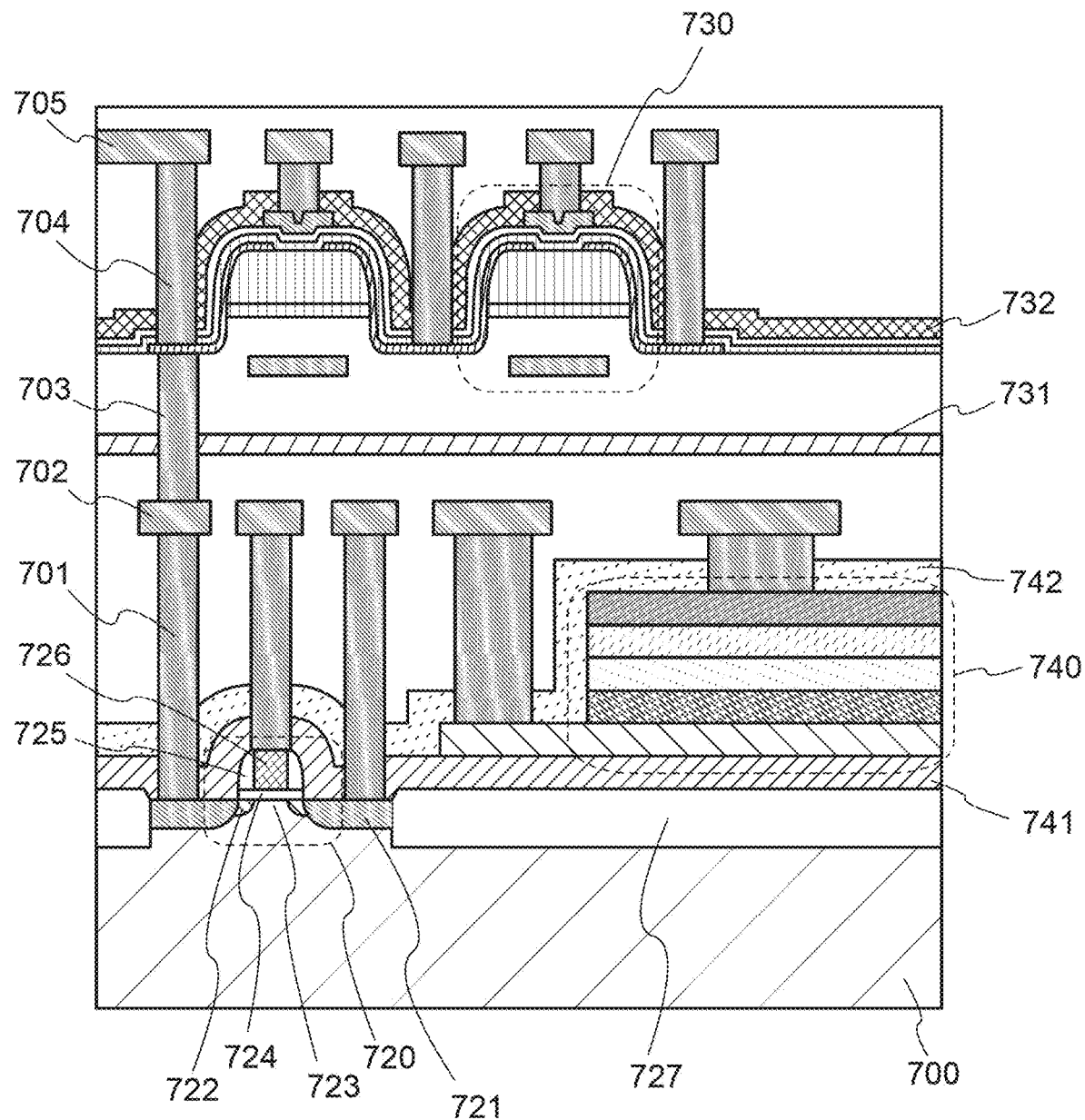
FIG. 4 is a cross-sectional view of a semiconductor device of one embodiment of the present invention.

In FIGS. 2 to 4, regions where reference numerals and hatching patterns are not given show regions formed of an insulator. These regions can be formed using an insulator containing at least one of aluminum oxide, aluminum nitride oxide, magnesium oxide, silicon oxide, silicon oxynitride, silicon nitride oxide, silicon nitride, gallium oxide, germanium oxide, yttrium oxide, zirconium oxide, lanthanum oxide, neodymium oxide, hafnium oxide, tantalum oxide, and the like. Alternatively, in these regions, an organic resin such as a polyimide resin, a polyamide resin, an acrylic resin, a siloxane resin, an epoxy resin, or a phenol resin can be used.

The semiconductor device 1000 in FIG. 2 preferably includes a cooling device such as a heat sink, a water-cooling cooler, or a cooling fan over the battery 740. The provision of the cooling device can prevent a malfunction of the semiconductor device 1000 caused by heat generation of the battery 740.

Figure 16:
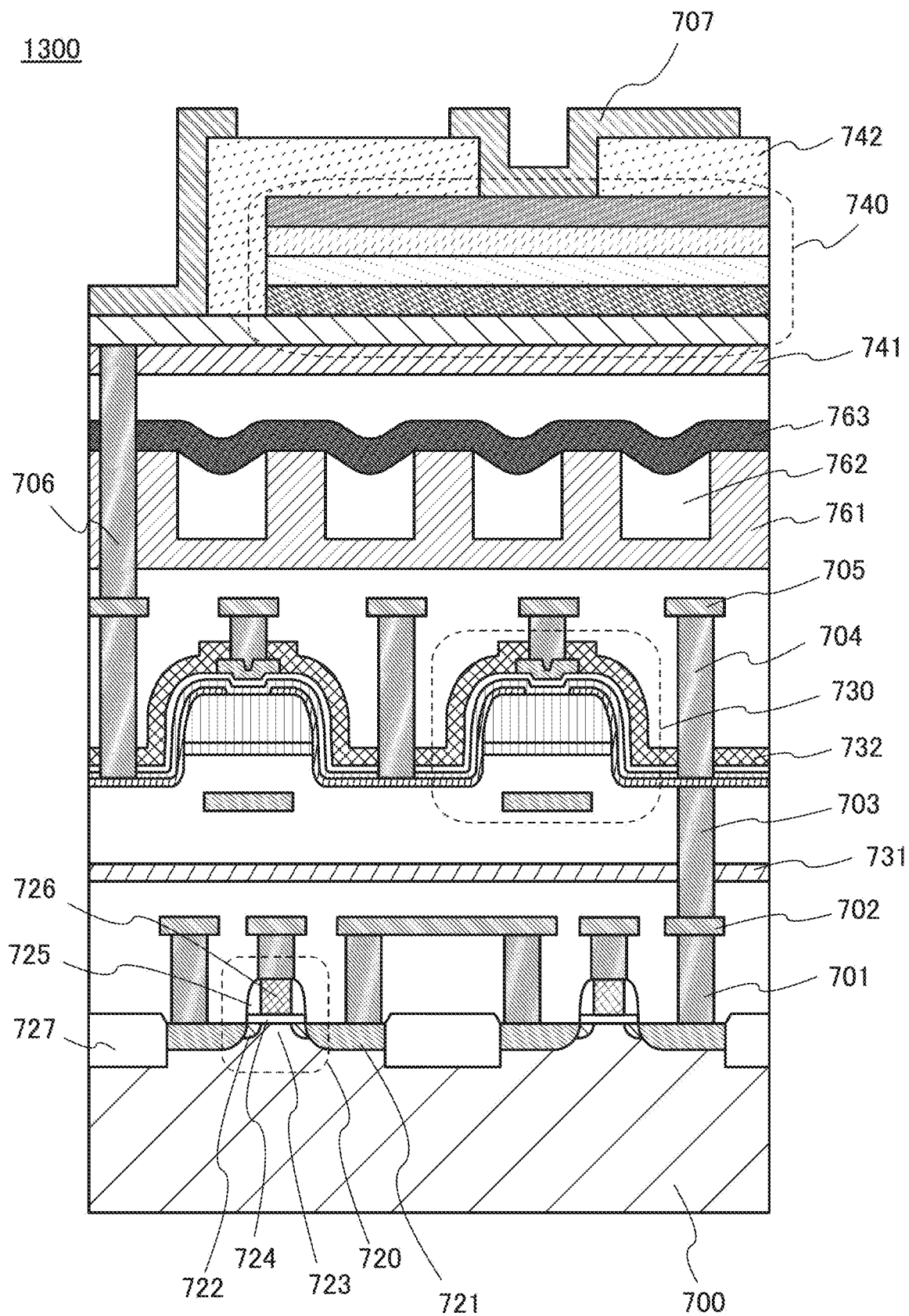
FIG. 16 is a cross-sectional view of a semiconductor device of one embodiment of the present invention.

The semiconductor device 1000 in FIG. 2 may include an air gap (a space of a vacuum layer) between the battery 740 and the transistor 730. The cross-sectional view of such a case is shown in FIG. 16. A semiconductor device 1300 shown in FIG. 16 includes an air gap 762 between the battery 740 and the transistor 730. The air gap 762 can be formed by forming an insulating film 763 having low coverage over an insulating film 761 having a trench. For each of the insulating films 761 and 763, an insulator including one or more of the following can be used: aluminum oxide, aluminum nitride oxide, silicon oxide, silicon oxynitride, silicon nitride oxide, silicon nitride, and the like. The provision of the air gap 762 under the battery 740 can prevent heat generated in the battery 740 from being conducted to the transistor 730 and the transistor 720. Thus, malfunctions of the transistor 720 and the transistor 730 caused by heat can be prevented.

Although the battery 740 is provided over the transistor 720 and the transistor 730 in FIG. 2, the battery 740 may be provided between the transistor 720 and the transistor 730. In that case, the transistor 720, the battery 740, and the transistor 730 are formed in this order. In the case where formation of the battery 740 requires heat treatment at such a high temperature as will destroy the transistor 730 in particular, it is preferable to form the transistor 730 after forming the battery 740.

The circuits of the CPU 11 or the regulators 13, 18, and 24 included in the device 10 in FIG. 1 are fabricated using the transistor 720 and the transistor 730, and the battery 740 that supplies power to the circuits is fabricated over the same substrate as that of the circuits, for example, whereby the device 10 can be reduced in size or thickness.

Structural Example 2 of Semiconductor Device

Although the transistor 720 in FIG. 2 is a planar transistor, the form of the transistor 720 is not limited thereto. For example, a FIN-type transistor, a TRI-GATE transistor or the like can be used. An example of a cross-sectional view in that case is shown in FIG. 3.

A semiconductor device 1100 shown in FIG. 3 is different from the semiconductor device 1000 in FIG. 2 in that it includes FIN-type transistors 750 provided over the substrate 700. In FIG. 3, the transistor 750 on the left side is a cross-sectional view in the channel length direction of the transistor, and the transistor 750 on the right side is a cross-sectional view in the channel width direction of the transistor.

In FIG. 3, an insulating film 757 is provided over the substrate 700. The substrate 700 includes a protruding portion with a thin tip (also referred to a fin). Note that an insulating film may be provided over the protruding portion. The insulating film functions as a mask for preventing the substrate 700 from being etched when the projecting portion is formed. Alternatively, the protruding portion may not have the thin tip; a protruding portion with a cuboid-like protruding portion and a protruding portion with a thick tip are permitted, for example. A gate insulating film 754 is provided over the protruding portion of the substrate 700, and a gate electrode 756 and a sidewall insulating layer 755 are formed thereover. In the substrate 700, an impurity region 751 functioning as a source region or a drain region, an impurity region 752 functioning as an LDD region or an extension region, and a channel region 753 are formed. Note that here is shown an example in which the substrate 700 includes the protruding portion; however, a semiconductor device of one embodiment of the present invention is not limited thereto. For example, a semiconductor region having a protruding portion may be formed by processing an SOI substrate.

For the other components of the semiconductor device 1100, the description of the semiconductor device 1000 is referred to.

Structure Example 3 of Semiconductor Device

A semiconductor device 1200 shown in FIG. 4 is different from the semiconductor device 1000 in FIG. 2 in that the battery 740 is below the transistor 730.

For the semiconductor device 1200 having the structure shown in FIG. 4, plugs and wirings connected to the transistor 720 can be formed at the same time as plugs and wirings connected to the battery 740, whereby the process can be simplified. Furthermore, in the case where formation of the battery 740 requires heat treatment at such a high temperature as will destroy the plug 701 or the wiring 702, the plug 701 and the wiring 702 need to be formed after the battery 740 is formed. In that case, it is preferable to provide the transistor 720 and the battery 740 at the same level as shown in FIG. 4.

In FIG. 4, the battery 740 is formed after the transistor 720 is formed; however, the transistor 720 may be formed after the battery 740 is formed first. In the case where formation of the battery 740 requires heat treatment at such a high temperature as will destroy the transistor 720 in particular, it is preferable to form the battery 740 first and then form the transistor 720.

For the other components of the semiconductor device 1200, the description of the semiconductor device 1000 is referred to.

The structures and methods described in this embodiment can be implemented by being combined as appropriate with any of the other structures and methods described in the other embodiments.

Embodiment 2

In this embodiment, the details and structural examples of the battery mentioned in Embodiment 1 will be described with reference to drawings.

Structural Example 1 of Battery

Figure 5A:
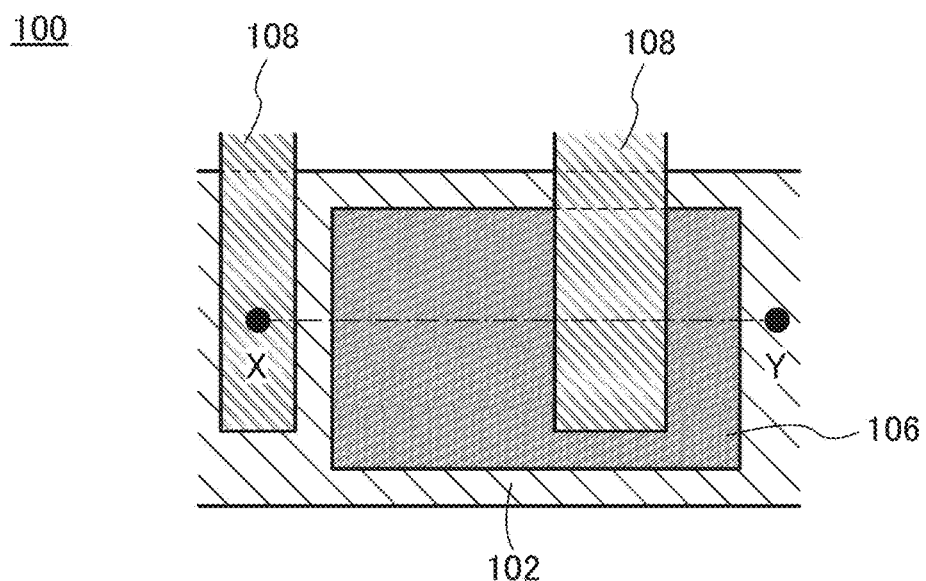
FIGS. 5A and 5B are a top view and a cross-sectional view, respectively, illustrating one embodiment of the present invention.
Figure 5B:
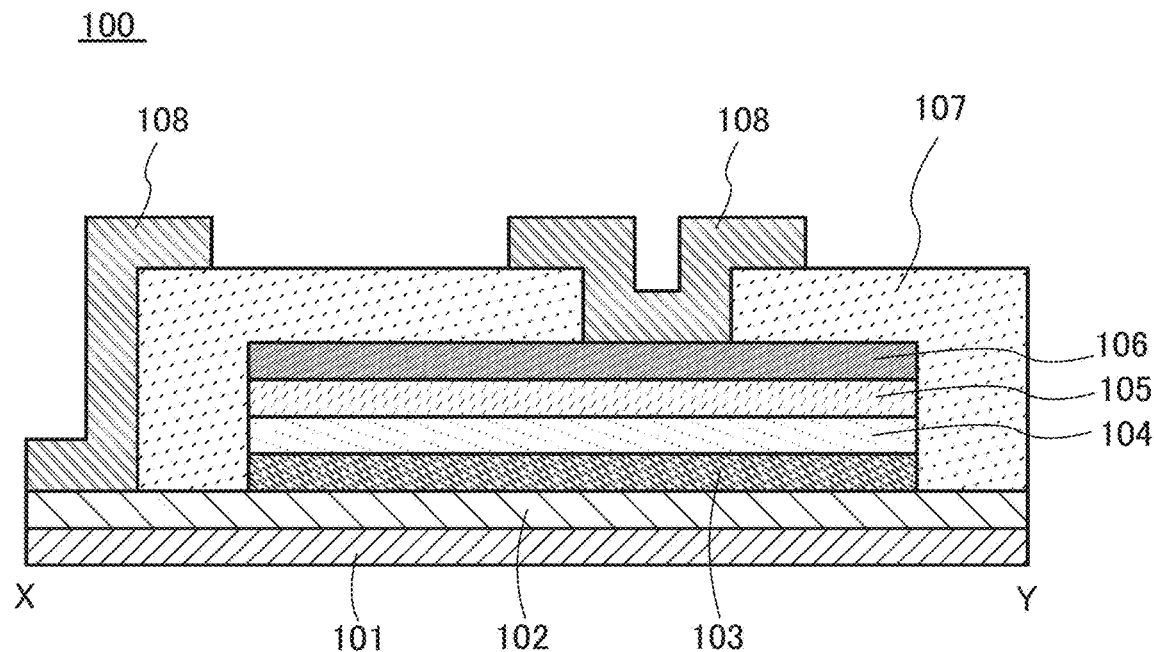

FIG. 5A is a top view of a battery 100, and FIG. 5B shows a cross-sectional view taken along a dashed-dotted line X-Y in FIG. 5A. In FIG. 5A, some components are enlarged, reduced in size, or omitted for easy understanding.

The battery 100 shown in FIG. 5A includes an insulating film 101, a positive electrode current collector layer 102 over the insulating film 101, a positive electrode active material layer 103 over the positive electrode current collector layer 102, a solid electrolyte layer 104 over the positive electrode active material layer 103, a negative electrode active material layer 105 over the solid electrolyte layer 104, and a negative electrode current collector layer 106 over the negative electrode active material layer 105. The positive electrode current collector layer 102 and the positive electrode active material layer 103 function as a positive electrode, and the negative electrode current collector layer 106 and the negative electrode active material layer 105 function as a negative electrode. In addition, an insulating film 107 is formed over the negative electrode current collector layer 106, and a wiring 108 is formed in an opening portion of the insulating film 107. The wiring 108 is electrically connected to the positive electrode current collector layer 102 or the negative electrode current collector layer 106.

Although not shown in the drawing, a lithium layer may be formed at the interface between the solid electrolyte layer 104 and the positive electrode active material layer 103 or at the interface between the solid electrolyte layer 104 and the negative electrode active material layer 105. The lithium layer is for supplying (or predoping) lithium serving as a carrier to the positive electrode active material layer or the negative electrode active material layer in the battery 100. The lithium layer may be formed over the entire surface of a layer over which the lithium layer is to be formed. Furthermore, a copper layer or a nickel layer may be formed in contact with the lithium layer. The copper layer or the nickel layer has a shape substantially the same as that of the lithium layer. The copper layer or the nickel layer can function as a current collector when the positive electrode active material layer or the negative electrode active material layer is predoped with lithium from the lithium layer.

Note that the predoping may be performed so that all the lithium included in the lithium layer is doped to the positive electrode active material layer or the negative electrode active material layer or so that part of the lithium layer is left after the predoping. The part of the lithium layer left after the predoping can be used to compensate lithium lost by irreversible capacity due to charge and discharge of the battery.

For the details of the insulating film 101, the description regarding the insulating film 741 in Embodiment 1 may be referred to.

The positive electrode current collector layer 102, the positive electrode active material layer 103, the negative electrode active material layer 105, and the negative electrode current collector layer 106 can be formed by a sputtering method, a CVD method, nanoimprint lithography, an evaporation method, or the like. When a sputtering method is used, it is preferable to use a DC power supply rather than an RF power supply for deposition. A sputtering method using a DC power supply is preferable because the deposition rate is high and thus cycle time is short. The thickness of each of the positive electrode current collector layer 102, the positive electrode active material layer 103, the negative electrode active material layer 105, and the negative electrode current collector layer 106 may be greater than or equal to 100 nm and less than or equal to 100 µm, for example.

The positive electrode current collector layer 102 may be formed to have a single-layer or layered structure using one or more of titanium (Ti), aluminum (Al), gold (Au), and platinum (Pt). Alternatively, a single-layer or layered conductive film including an alloy of the above metals or a compound containing any of these as a main component may be used.

The positive electrode active material layer 103 may be formed to have a single-layer or layered structure using one or more of lithium cobaltate, lithium iron phosphate, lithium manganite, lithium nickelate, and vanadium oxide.

Furthermore, the positive electrode active material layer 103 may be formed using an olivine-type lithium-containing complex phosphate. Typical examples of a lithium-containing complex phosphate ($LiMPO_4$ (general formula) (M is one or more of Fe(II), Mn(II), Co(II), and Ni(II))) are $LiFePO_4$, $LiNiPO_4$, $LiCoPO_4$, $LiMnPO_4$, $LiFe_aNi_bPO_4$, $LiFe_aCo_bPO_4$, $LiFe_aMn_bPO_4$, $LiNi_aCo_bPO_4$, $LiNi_aMn_bPO_4$ ($a+b \leq 1$, $0<a<1$, and $0<b<1$), $LiFe_cNi_dCo_ePO_4$, $LiFe_cNi_dMn_ePO_4$, $LiNi_cCo_dMn_ePO_4$ ($c+d+e \leq 1$, $0<c<1$, $0<d<1$, and $0<e<1$), and $LiFe_fNi_gCo_hMn_iPO_4$ ($f+g+h+i \leq 1$, $0<f<1$, $0<g<1$, $0<h<1$, and $0<i<1$).

An inorganic solid electrolyte that can be formed by a sputtering method, an evaporation method, or a CVD method is used for the solid electrolyte layer 104. Examples of the inorganic solid electrolyte are a sulfide-based solid electrolyte and an oxide-based solid electrolyte.

Examples of the sulfide-based solid electrolyte are lithium complex sulfide materials such as $Li_7P_3S_{11}$, $Li_{3.25}P_{0.95}S_4$, $Li_{10}GeP_2S_{12}$, $Li_{3.25}Ge_{0.25}P_{0.75}S_4$, $Li_2S$—$P_2S_5$, $Li_2S$—$GeS_2$, $Li_2S$—$SiS_2$—$Li_3PO_4$, $Li_2S$—$SiS_2$—$Ga_2S_3$, $Li_2S$—$SiS_2$—$Li_4SiO_4$, $LiI$—$Li_2S$—$P_2S_5$, $LiI$—$Li_2S$—$B_2S_3$, and $LiI$—$Li_2S$—$SiS_2$.

Examples of the oxide-based solid electrolyte are lithium complex oxides and lithium oxide materials, such as $Li_{1.3}Al_{0.3}Ti_{1.7}(PO_4)_3$, $Li_{1.07}Al_{0.69}Ti_{1.46}(PO_4)_3$, $Li_4SiO_4$—$Li_3BO_3$, $Li_{2.9}PO_{3.3}N_{0.46}$, $Li_{3.6}Si_{0.6}P_{0.4}O_4$, $Li_{1.5}Al_{0.5}Ge_{1.6}(PO_4)_3$, $Li_2O$, $Li_2CO_3$, $Li_2MoO_4$, $Li_3PO_4$, $Li_3VO_4$, $Li_4SiO_4$, LLT($La_{2/3-x}Li_{3x}TiO_3$), and LLZ($Li_7La_3Zr_2O_{12}$).

Alternatively, a polymer solid electrolyte such as polyethylene oxide (PEO) formed by a coating method or the like may be used for the solid electrolyte layer 104. Still alternatively, a composite solid electrolyte containing any of the above inorganic solid electrolytes and a polymer solid electrolyte may be used.

A separator may be provided in the solid electrolyte layer 104 to prevent short-circuiting between the positive electrode and the negative electrode, as necessary. As the separator, an insulator with pores is preferably used. For example, cellulose; a glass fiber; ceramics; or a synthetic fiber containing nylon (polyamide), vinylon (polyvinyl alcohol based fiber), polyester, acrylic, polyolefin, or polyurethane; can be used.

The negative electrode active material layer 105 may be formed to have a single-layer or layered structure using one or more of carbon (C), silicon (Si), germanium (Ge), tin (Sn), aluminum (Al), lithium (Li), lithium titanium oxide, lithium niobate, niobium oxide, tantalum oxide, and silicon oxide.

The negative electrode current collector layer 106 may be formed to have a single-layer or layered structure using one or more of titanium (Ti), copper (Cu), stainless steel, iron (Fe), gold (Au), platinum (Pt), and nickel (Ni). Alternatively, a single-layer or layered conductive film including an alloy of the above metals or a compound containing any of these as a main component may be used.

The positive electrode active material layer 103 and the negative electrode active material layer 105 may each include a binder for improving adhesion of active materials as necessary.

It is preferable for the binder to include, for example, water-soluble polymers. As the water-soluble polymers, a polysaccharide or the like can be used. As the polysaccharide, a cellulose derivative such as carboxymethyl cellulose (CMC), methyl cellulose, ethyl cellulose, hydroxypropyl cellulose, diacetyl cellulose, or regenerated cellulose, starch, or the like can be used.

As the binder, a rubber material such as styrene-butadiene rubber (SBR), styrene-isoprene-styrene rubber, acrylonitrile-butadiene rubber, butadiene rubber, or ethylene-propylene-diene copolymer is preferably used. Any of these rubber materials is more preferably used in combination with the aforementioned water-soluble polymers.

Alternatively, as the binder, a material such as polystyrene, poly(methyl acrylate), poly(methyl methacrylate) (PMMA), sodium polyacrylate, polyvinyl alcohol (PVA), polyethylene oxide (PEO), polypropylene oxide, polyimide, polyvinyl chloride, polytetrafluoroethylene, polyethylene, polypropylene, isobutylene, polyethylene terephthalate, nylon, polyvinylidene fluoride (PVDF), or polyacrylonitrile (PAN) can be preferably used.

Two or more of the above materials may be used in combination for the binder.

Furthermore, the positive electrode active material layer 103 and the negative electrode active material layer 105 may each include a conductive additive or the like for improving the conductivity of the active material layers.

Examples of the conductive additive include natural graphite, artificial graphite such as mesocarbon microbeads, and carbon fiber. Examples of carbon fiber include mesophase pitch-based carbon fiber, isotropic pitch-based carbon fiber, carbon nanofiber, and carbon nanotube. Carbon nanotube can be formed by, for example, a vapor deposition method. Other examples of the conductive additive include carbon materials such as carbon black (acetylene black (AB)) and graphene. Alternatively, metal powder or metal fibers of copper, nickel, aluminum, silver, gold, or the like, a conductive ceramic material, or the like can be used.

Flaky graphene has an excellent electrical characteristic of high conductivity and excellent physical properties of high flexibility and high mechanical strength. Thus, the use of graphene as the conductive additive can increase contact points and the contact area of active materials.

Note that graphene in this specification includes single-layer graphene and multilayer graphene including two to hundred layers. Single-layer graphene refers to a one-atom-thick sheet of carbon molecules having $\pi$ bonds. Graphene oxide refers to a compound formed by oxidation of such graphene. When graphene oxide is reduced to form graphene, oxygen contained in the graphene oxide is not entirely released and part of the oxygen remains in the graphene. In the case where graphene contains oxygen, the proportion of the oxygen measured by X-ray photoelectron spectroscopy (XPS) is higher than or equal to 2% and lower than or equal to 20%, preferably higher than or equal to 3% and lower than or equal to 15% of the whole graphene.

For the details of the insulating film 107, the description regarding the insulating film 742 in Embodiment 1 may be referred to.

For the details of the wiring 108, the description regarding the wiring 707 in Embodiment 1 may be referred to.

For the battery 100, the positions of the positive electrode and the negative electrode shown in FIG. 5B may be reversed. That is to say, the negative electrode current collector layer 106, the negative electrode active material layer 105, the solid electrolyte layer 104, the positive electrode active material layer 103, and the positive electrode current collector layer 102 may be formed in this order from the bottom.

For example, in the case where $LiFePo_4$ with a thickness of 1 μm is used for the positive electrode active material layer 103, the capacity of the battery 100 obtained by calculation is approximately 60 μAh/cm$^2$.

For example, in the case where $LiCoO_2$ with a thickness of 1 μm is used for the positive electrode active material layer 103, the capacity of the battery 100 obtained by calculation is approximately 70 μAh/cm².

For example, in the case where $LiMn_2O_4$ with a thickness of 1 μm is used for the positive electrode active material layer 103, the capacity of the battery 100 obtained by calculation is approximately 60 μAh/cm².

Note that each of the above calculations uses the theoretical capacity of the positive electrode active material (i.e., 170 mAh/g for $LiFePo_4$, 137 mAh/g for $LiCoO_2$, and 148 mAh/g for $LiMn_2O_4$), supposing that lithium is used for the negative electrode active material layer 105.

The area and capacity of the battery 100 may be determined in accordance with the amount of electric power required for a semiconductor device or electronic device to be connected. In the case where $LiFePo_4$ is used for the positive electrode active material layer 103, for example, by making the area of the battery 100 (the area where the positive electrode active material layer 103 and the negative electrode active material layer 105 overlap with each other) greater than or equal to 1 cm² and less than or equal to 100 cm², the capacity of the battery 100 can be greater than or equal to 60 μAh and less than or equal to 6 mAh, according to the above calculation results.

Furthermore, in accordance with the amount of electric power required for a semiconductor device or electronic device connected to the battery, a plurality of batteries 100 may be connected in series and/or in parallel. In particular, connecting a plurality of stacked batteries 100 in series and/or in parallel is preferable because the energy density of the battery can be increased while the area occupied by the battery can be reduced.

Structural Example 2 of Battery

Figure 6A:
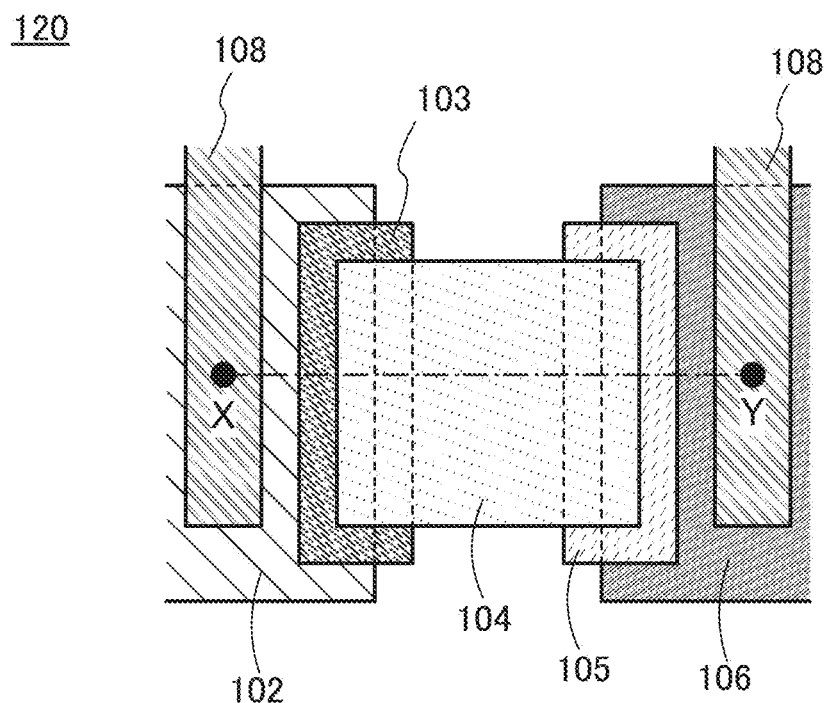
FIGS. 6A and 6B are a top view and a cross-sectional view, respectively, illustrating one embodiment of the present invention.
Figure 6B:
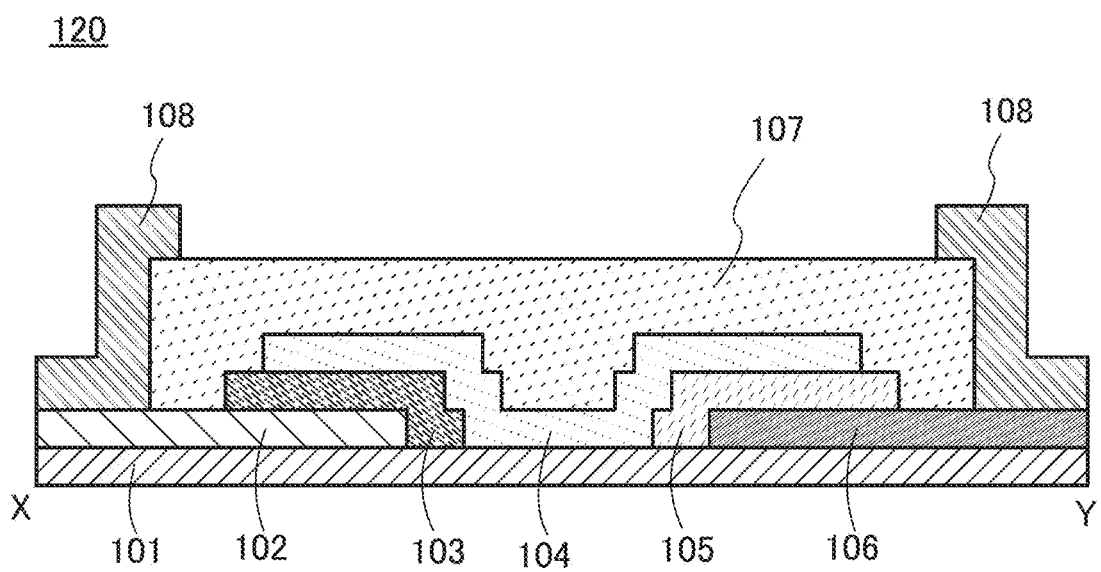

FIGS. 6A and 6B show an example of the battery included in one embodiment of the present invention. FIG. 6A is a top view of a battery 120, and FIG. 6B shows a cross-sectional view taken along a dashed-dotted line X-Y in FIG. 6A. In FIG. 6A, some components are enlarged, reduced in size, or omitted for easy understanding.

The battery 120 shown in FIG. 6B includes an insulating film 101; a positive electrode current collector layer 102 and a negative electrode current collector layer 106, which are level with each other and are arranged over the insulating film 101; a positive electrode active material layer 103 over the positive electrode current collector layer 102; a negative electrode active material layer 105 over the negative electrode current collector layer 106; and a solid electrolyte layer 104 in contact with at least the positive electrode active material layer 103 and the negative electrode active material layer 105. The positive electrode current collector layer 102 and the positive electrode active material layer 103 function as a positive electrode, and the negative electrode current collector layer 106 and the negative electrode active material layer 105 function as a negative electrode. In addition, an insulating film 107 is formed over the solid electrolyte layer 104, and a wiring 108 is formed in an opening portion of the insulating film 107. The wiring 108 is electrically connected to the positive electrode current collector layer 102 or the negative electrode current collector layer 106.

The battery 120 is different from the battery 100 in FIGS. 5A and 5B in that the positive electrode current collector layer 102 and the negative electrode current collector layer 106 are level with each other and the positive electrode and the negative electrode exist in the X-Y direction of FIG. 6B.

The structure of the battery 120 shown in FIG. 6B makes it possible to provide a certain distance between the positive electrode and the negative electrode, whereby short-circuiting between the positive electrode and the negative electrode can be prevented.

For the details regarding the components of the battery 120, the description of the battery 100 in FIGS. 5A and 5B may be referred to.

The positive electrode current collector layer 102 and the negative electrode current collector layer 106 in the battery 120 may be formed using the same materials, at a time. Formation of the positive and negative electrode current collector layers using the same materials at a time can simplify the manufacturing process.

Structural Example 3 of Battery

Figure 7A:
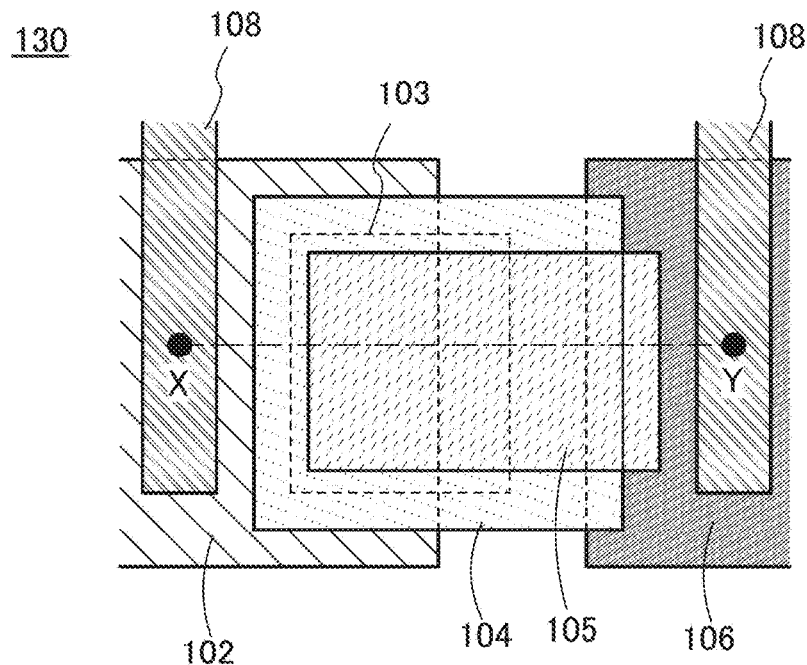
FIGS. 7A and 7B are a top view and a cross-sectional view, respectively, illustrating one embodiment of the present invention.
Figure 7B:
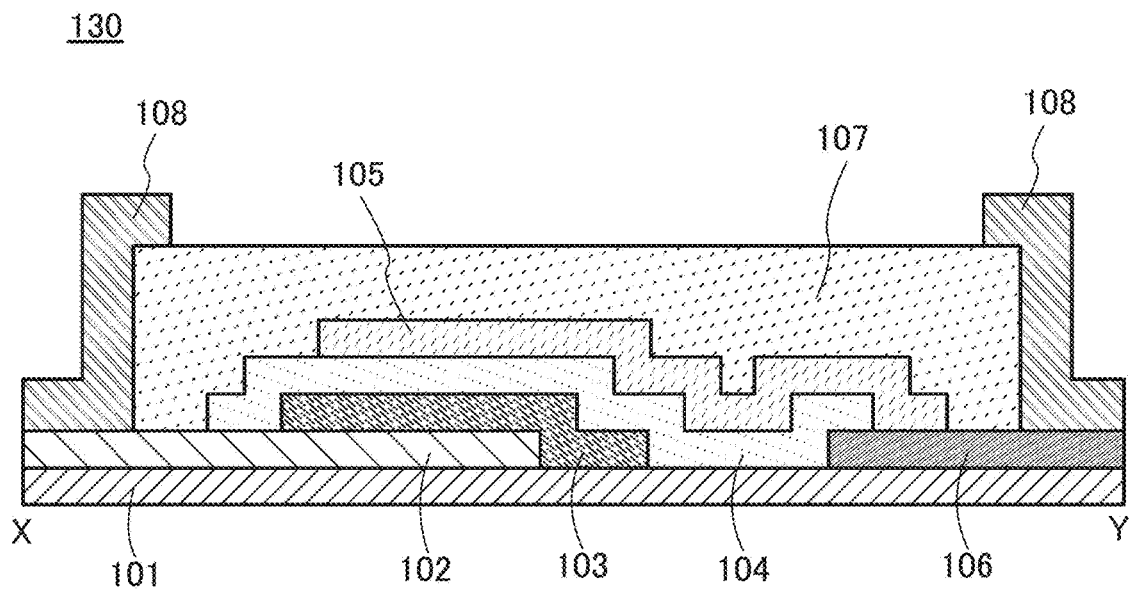

FIGS. 7A and 7B show an example of the battery included in one embodiment of the present invention. FIG. 7A is a top view of a battery 130, and FIG. 7B shows a cross-sectional view taken along a dashed-dotted line X-Y in FIG. 7A. In FIG. 7A, some components are enlarged, reduced in size, or omitted for easy understanding.

The battery 130 shown in FIG. 7B includes an insulating film 101; a positive electrode current collector layer 102 and a negative electrode current collector layer 106, which are level with each other and are arranged over the insulating film 101; a positive electrode active material layer 103 over the positive electrode current collector layer 102; a solid electrolyte layer 104 over the positive electrode active material layer 103, the insulating film 101, and the negative electrode current collector layer 106; and a negative electrode active material layer 105, which overlaps with part of the positive electrode active material layer 103 with the solid electrolyte layer 104 positioned therebetween and is arranged over the solid electrolyte layer 104 and the negative electrode current collector layer 106. The positive electrode current collector layer 102 and the positive electrode active material layer 103 function as a positive electrode, and the negative electrode current collector layer 106 and the negative electrode active material layer 105 function as a negative electrode. In addition, an insulating film 107 is formed over the negative electrode active material layer 105, and a wiring 108 is formed in an opening portion of the insulating film 107. The wiring 108 is electrically connected to the positive electrode current collector layer 102 or the negative electrode current collector layer 106.

The battery 130 shown in FIG. 7B is different from the battery 120 shown in FIG. 6B in that the negative electrode active material layer 105 is formed over the solid electrolyte layer 104. The structure of the battery 130 shown in FIG. 7B makes it possible to provide a certain distance between the positive electrode current collector layer 102 and the negative electrode current collector layer 106 for preventing short-circuiting, and to shorten the distance between the positive electrode active material layer 103 and the negative electrode active material layer 105 for facilitating the efficient movement of ions.

For the details regarding the components of the battery 130, the description of the battery 100 in FIGS. 5A and 5B may be referred to.

For the battery 130, the positions of the positive electrode and the negative electrode may be interchanged. That is to say, the positions of the positive electrode current collector layer 102 and the positive electrode active material layer 103 may be interchanged with the positions of the negative electrode current collector layer 106 and the negative electrode active material layer 105.

Furthermore, the positive electrode current collector layer 102 and the negative electrode current collector layer 106 in the battery 130 may be formed through the same step. Formation of the positive and negative electrode current collector layers through the same step can simplify the manufacturing process.

Structural Example 4 of Battery

Figure 8A:
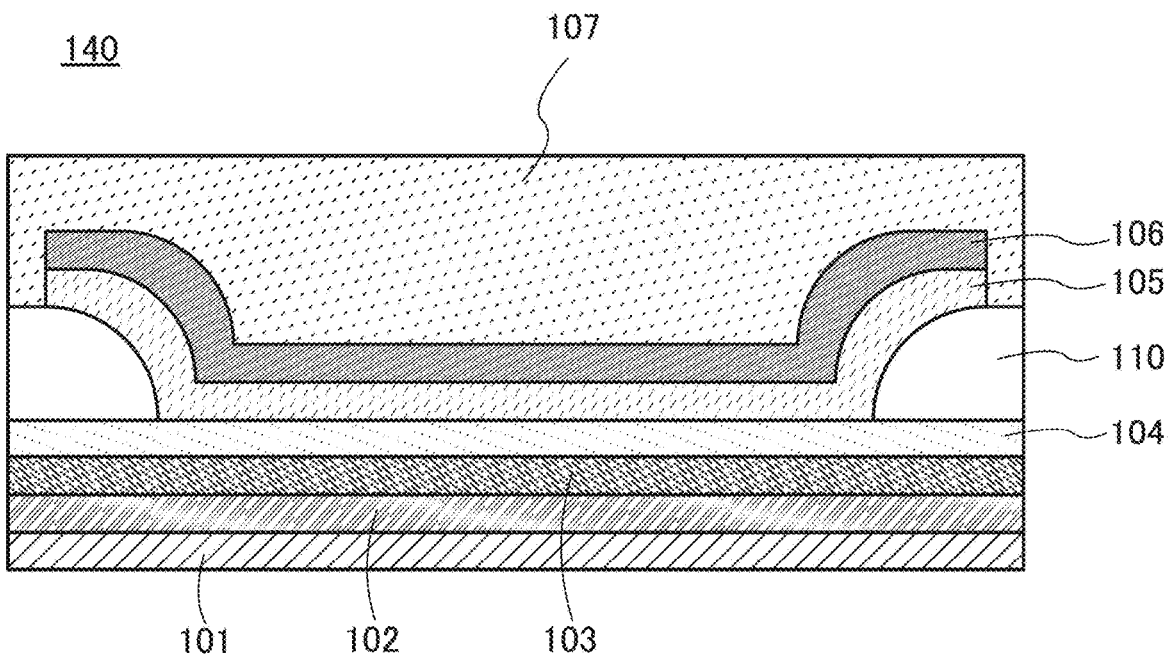
FIGS. 8A and 8B are each a cross-sectional view of a battery of one embodiment of the present invention.
Figure 8B:
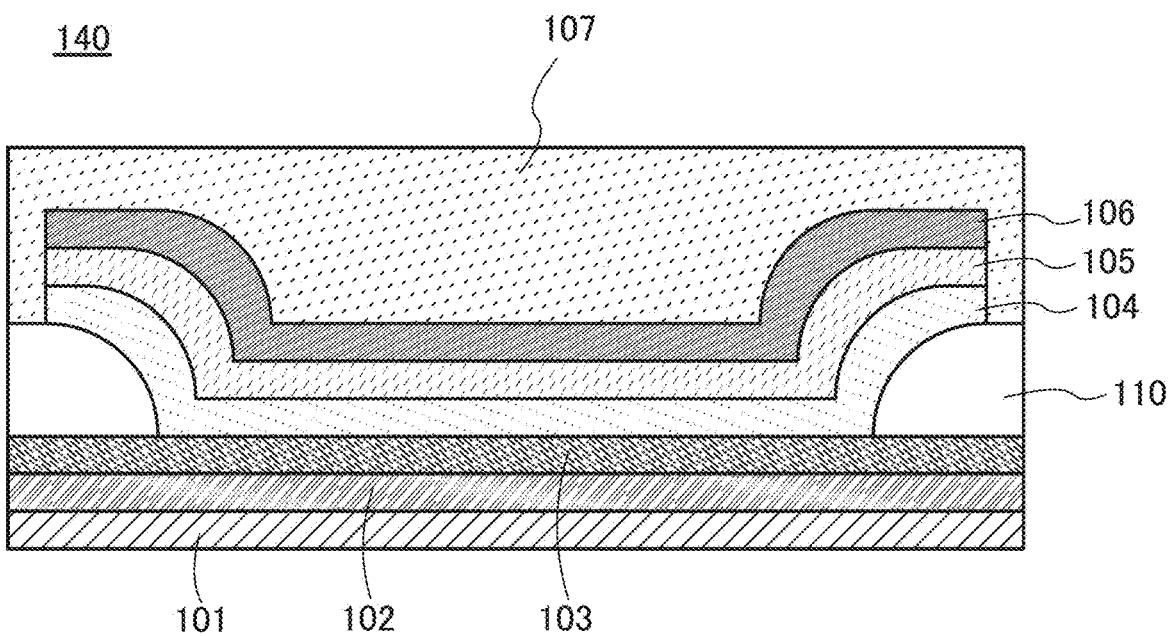

An example of the battery included in one embodiment of the present invention is shown in each of FIGS. 8A and 8B. FIG. 8A is a cross-sectional view of a battery 140.

The battery 140 shown in FIG. 8A includes an insulating film 101, a positive electrode current collector layer 102 over the insulating film 101, a positive electrode active material layer 103 over the positive electrode current collector layer 102, a solid electrolyte layer 104 over the positive electrode active material layer 103, an insulating film 110 over the solid electrolyte layer 104, a negative electrode active material layer 105 over the solid electrolyte layer 104 and the insulating film 110, and a negative electrode current collector layer 106 over the negative electrode active material layer 105. The positive electrode current collector layer 102 and the positive electrode active material layer 103 function as a positive electrode, and the negative electrode current collector layer 106 and the negative electrode active material layer 105 function as a negative electrode. In addition, an insulating film 107 is formed over the negative electrode current collector layer 106. Although not shown in the drawing, the positive electrode current collector layer 102 and the negative electrode current collector layer 106 are each electrically connected to an external device via a wiring.

The battery 140 shown in FIG. 8A has a region where the insulating film 110 exists between the solid electrolyte layer 104 and the negative electrode active material layer 105. The insulating film 110 has a function of preventing short-circuiting between the positive electrode and the negative electrode.

The insulating film 110 can be formed using, for example, an organic resin or an inorganic insulating material. As the organic resin, for example, a polyimide resin, a polyamide resin, an acrylic resin, a siloxane resin, an epoxy resin, or a phenol resin can be used. As the inorganic insulating material, silicon oxide, silicon oxynitride, or the like can be used. In particular, a photosensitive resin is preferably used for easy formation of the insulating film 110. There is no particular limitation on the method for forming the insulating film 110. A photolithography method, a sputtering method, an evaporation method, a droplet discharging method (e.g., an inkjet method), a printing method (e.g., a screen printing method or an offset printing method), or the like can be used.

For the other components of the battery 140, the description of the battery 100 in FIGS. 5A and 5B may be referred to.

In the battery 140, the insulating film 110 may be formed over the positive electrode active material layer 103 as shown in FIG. 8B.

For the battery 140 shown in FIGS. 8A and 8B, the positions of the positive electrode and the negative electrode may be reversed. That is to say, the negative electrode current collector layer 106, the negative electrode active material layer 105, the solid electrolyte layer 104, the positive electrode active material layer 103, and the positive electrode current collector layer 102 may be formed in this order from the bottom.

The structures and methods described in this embodiment can be implemented by being combined as appropriate with any of the other structures and methods described in the other embodiments.

Embodiment 3

In this embodiment, the oxide semiconductor transistor mentioned in Embodiment 1 will be described with reference to drawings. Note that the oxide semiconductor transistor described in this embodiment is an example, and the form of a transistor that can be used for the invention is not limited thereto.

Structural Example of Oxide Semiconductor Transistor

Figure 9A:
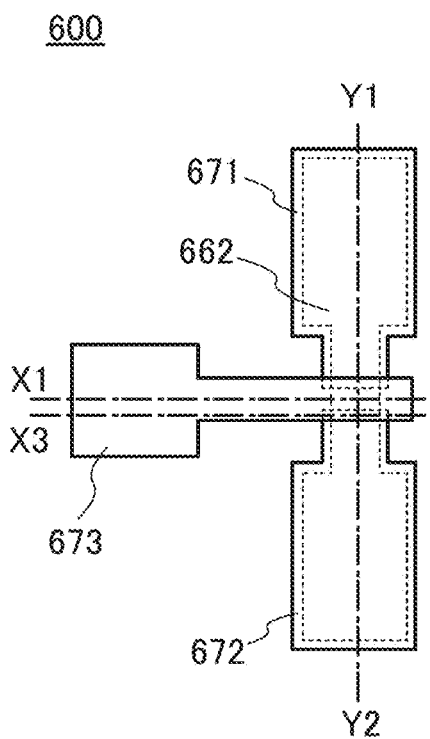
FIG. 9A is a top view and FIGS. 9B to 9D are cross-sectional views of a transistor included in one embodiment of the present invention.
Figure 9B:
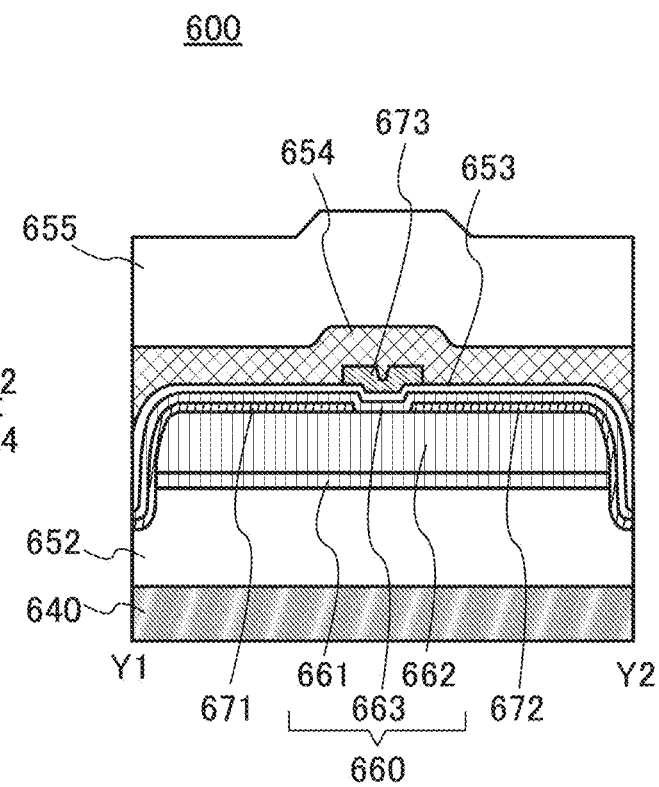
Figure 9C:
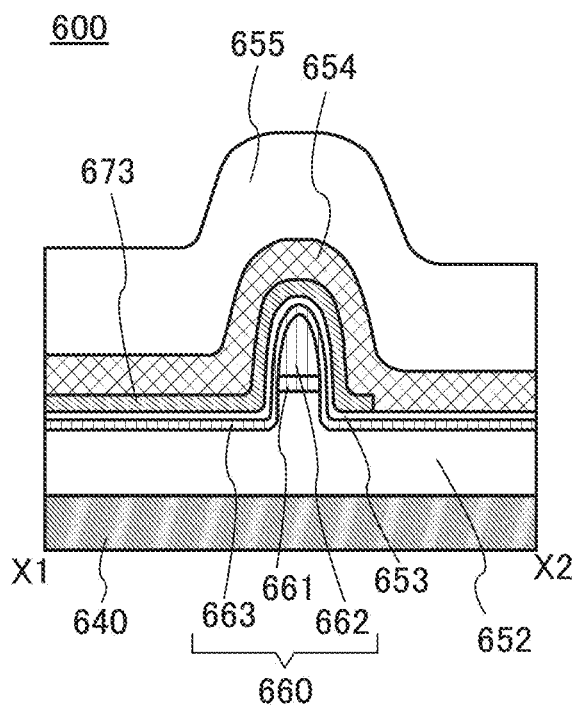
Figure 9D:
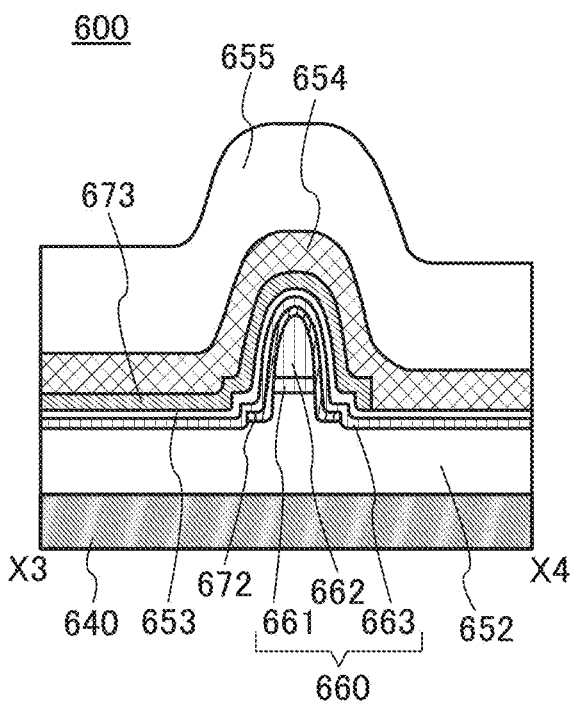

FIGS. 9A to 9D are a top view and cross-sectional views of a transistor 600. FIG. 9A is the top view. FIG. 9B corresponds to a cross section along the dashed-dotted line Y1-Y2 in FIG. 9A. FIG. 9C corresponds to a cross section along the dashed-dotted line X1-X2 in FIG. 9A. FIG. 9D corresponds to a cross section along the dashed-dotted line X3-X4 in FIG. 9A. In FIGS. 9A to 9D, some components are scaled up or down or omitted for easy understanding. In some cases, the direction of the dashed-dotted line Y1-Y2 is referred to as a channel length direction and the direction of the dashed-dotted line X1-X2 is referred to as a channel width direction.

Note that the channel length refers to, for example, a distance between a source (a source region or a source electrode) and a drain (a drain region or a drain electrode) in a region where a semiconductor (or a portion where a current flows in a semiconductor when a transistor is on) and a gate electrode overlap with each other or a region where a channel is formed in a top view of the transistor. In one transistor, channel lengths in all regions are not necessarily the same. In other words, the channel length of one transistor is not limited to one value in some cases. Therefore, in this specification, the channel length is any one of values, the maximum value, the minimum value, or the average value in a region where a channel is formed.

A channel width refers to, for example, the length of a portion where a source and a drain face each other in a region where a semiconductor (or a portion where a current flows in a semiconductor when a transistor is on) and a gate electrode overlap with each other, or a region where a channel is formed. In one transistor, channel widths in all regions are not necessarily the same. In other words, the channel width of one transistor is not limited to one value in some cases. Therefore, in this specification, the channel width is any one of values, the maximum value, the minimum value, or the average value in a region where a channel is formed.

Note that depending on transistor structures, a channel width in a region where a channel is formed actually (hereinafter referred to as an effective channel width) is different from a channel width shown in a top view of a transistor (hereinafter referred to as an apparent channel width) in some cases. For example, in a transistor having a three-dimensional structure, an effective channel width is greater than an apparent channel width shown in a top view of the transistor, and its influence cannot be ignored in some cases. For example, in a miniaturized transistor having a three-dimensional structure, the proportion of a channel region formed in a top surface of a semiconductor is higher than the proportion of a channel region formed in a side surface of a semiconductor in some cases. In that case, an effective channel width obtained when a channel is actually formed is greater than an apparent channel width shown in the top view.

In a transistor having a three-dimensional structure, an effective channel width is difficult to measure in some cases. For example, to estimate an effective channel width from a design value, it is necessary to assume that the shape of a semiconductor is known as an assumption condition. Therefore, in the case where the shape of a semiconductor is not known accurately, it is difficult to measure an effective channel width accurately.

Therefore, in this specification, in a top view of a transistor, an apparent channel width that is a length of a portion where a source and a drain face each other in a region where a semiconductor and a gate electrode overlap with each other is referred to as a surrounded channel width (SCW) in some cases. Further, in this specification, in the case where the term "channel width" is simply used, it may denote a surrounded channel width and an apparent channel width. Alternatively, in this specification, in the case where the term "channel width" is simply used, it may denote an effective channel width in some cases. Note that the values of a channel length, a channel width, an effective channel width, an apparent channel width, a surrounded channel width, and the like can be determined by obtaining and analyzing a cross-sectional TEM image and the like.

Note that in the case where electric field mobility, a current value per channel width, and the like of a transistor are obtained by calculation, a surrounded channel width may be used for the calculation. In that case, a value different from one in the case where an effective channel width is used for the calculation is obtained in some cases.

The transistor 600 includes an insulating film 652 over a substrate 640; a stack in which an oxide semiconductor 661 and an oxide semiconductor 662 are formed in this order over the insulating film 652; a source electrode 671 and a drain electrode 672 electrically connected to part of the stack; an oxide semiconductor 663 that covers part of the stack, part of the source electrode 671, and part of the drain electrode 672; a gate insulating film 653 and a gate electrode 673 that cover part of the stack, part of the source electrode 671, part of the drain electrode 672, and the oxide semiconductor 663; an insulating film 654 over the source electrode 671, the drain electrode 672, and the gate electrode 673; and an insulating film 655 over the insulating film 654. Note that the oxide semiconductor 661, the oxide semiconductor 662, and the oxide semiconductor 663 are collectively referred to as an oxide semiconductor 660.

Note that at least part (or all) of the source electrode 671 (and/or the drain electrode 672) is provided on at least part (or all) of a surface, a side surface, a top surface, and/or a bottom surface of a semiconductor layer such as the oxide semiconductor 662 (and/or the oxide semiconductor 661).

Alternatively, at least part (or all) of the source electrode 671 (and/or the drain electrode 672) is in contact with at least part (or all) of a surface, a side surface, a top surface, and/or a bottom surface of a semiconductor layer such as the oxide semiconductor 662 (and/or the oxide semiconductor 661). Alternatively, at least part (or all) of the source electrode 671 (and/or the drain electrode 672) is in contact with at least part (or all) of a semiconductor layer such as the oxide semiconductor 662 (and/or the oxide semiconductor 661).

Alternatively, at least part (or all) of the source electrode 671 (and/or the drain electrode 672) is electrically connected to at least part (or all) of a surface, a side surface, a top surface, and/or a bottom surface of a semiconductor layer such as the oxide semiconductor 662 (and/or the oxide semiconductor 661). Alternatively, at least part (or all) of the source electrode 671 (and/or the drain electrode 672) is electrically connected to part (or all) of a semiconductor layer such as the oxide semiconductor 662 (and/or the oxide semiconductor 661).

Alternatively, at least part (or all) of the source electrode 671 (and/or the drain electrode 672) is provided near part (or all) of a surface, a side surface, a top surface, and/or a bottom surface of a semiconductor layer such as the oxide semiconductor 662 (and/or the oxide semiconductor 661). Alternatively, at least part (or all) of the source electrode 671 (and/or the drain electrode 672) is provided near part (or all) of a semiconductor layer such as the oxide semiconductor 662 (and/or the oxide semiconductor 661).

Alternatively, at least part (or all) of the source electrode 671 (and/or the drain electrode 672) is provided next to part (or all) of a surface, a side surface, a top surface, and/or a bottom surface of a semiconductor layer such as the oxide semiconductor 662 (and/or the oxide semiconductor 661). Alternatively, at least part (or all) of the source electrode 671 (and/or the drain electrode 672) is provided next to part (or all) of a semiconductor layer such as the oxide semiconductor 662 (and/or the oxide semiconductor 661).

Alternatively, at least part (or all) of the source electrode 671 (and/or the drain electrode 672) is provided obliquely above part (or all) of a surface, a side surface, a top surface, and/or a bottom surface of a semiconductor layer such as the oxide semiconductor 662 (and/or the oxide semiconductor 661). Alternatively, at least part (or all) of the source electrode 671 (and/or the drain electrode 672) is provided obliquely above part (or all) of a semiconductor layer such as the oxide semiconductor 662 (and/or the oxide semiconductor 661).

Alternatively, at least part (or all) of the source electrode 671 (and/or the drain electrode 672) is provided above part (or all) of a surface, a side surface, a top surface, and/or a bottom surface of a semiconductor layer such as the oxide semiconductor 662 (and/or the oxide semiconductor 661). Alternatively, at least part (or all) of the source electrode 671 (and/or the drain electrode 672) is provided above part (or all) of a semiconductor layer such as the oxide semiconductor 662 (and/or the oxide semiconductor 661).

Note that functions of a "source" and a "drain" of a transistor are sometimes replaced with each other when a transistor of opposite polarity is used or when the direction of current flowing is changed in circuit operation, for example. Therefore, the terms "source" and "drain" can be replaced with each other in this specification.

The transistor of one embodiment of the present invention has a top-gate structure with a channel length of greater than or equal to 10 nm and less than or equal to 1000 nm, preferably greater than or equal to 20 nm and less than or equal to 500 nm, further preferably greater than or equal to 30 nm and less than or equal to 300 nm.

Constituent elements of the semiconductor device of this embodiment will be described below in detail.

<Substrate>

The substrate 640 is not limited to a simple supporting substrate and may be a substrate where a device such as a transistor is formed. In that case, one of the gate electrode 673, the source electrode 671, and the drain electrode 672 of the transistor 600 may be electrically connected to the device.

<Base Insulating Film>

The insulating film 652 can have a function of supplying oxygen to the oxide semiconductor 660 as well as a function of preventing diffusion of impurities from the substrate 640. For this reason, the insulating film 652 preferably contains oxygen and more preferably has an oxygen content higher than that in the stoichiometric composition. For example, the insulating film 652 is a film in which the amount of released oxygen converted into oxygen atoms is $1.0 \times 10^{19}$ atoms/cm³ or more in thermal desorption spectroscopy (TDS) analysis. Note that the temperature of the film surface in the TDS analysis is preferably higher than or equal to 100° C. and lower than or equal to 700° C., or higher than or equal to 100° C. and lower than or equal to 500° C. When the substrate 640 is a substrate where a device is formed as described above, the insulating film 652 is preferably subjected to planarization treatment such as chemical mechanical polishing (CMP) treatment so as to have a flat surface.

The insulating film 652 can be formed using an oxide insulating film of aluminum oxide, aluminum oxynitride, magnesium oxide, silicon oxide, silicon oxynitride, gallium oxide, germanium oxide, yttrium oxide, zirconium oxide, lanthanum oxide, neodymium oxide, hafnium oxide, tantalum oxide, or the like, a nitride insulating film of silicon nitride, silicon nitride oxide, aluminum nitride oxide, or the like, or a film in which any of the above materials are mixed.

<Oxide Semiconductor>

Typical examples of the oxide semiconductor 660 are an In—Ga oxide, an In—Zn oxide, and In-M-Zn oxide (M represents Ti, Ga, Y, Zr, La, Ce, Nd, Sn, or Hf). In particular, In-M-Zn oxide (M represents Ti, Ga, Y, Zr, La, Ce, Nd, Sn, or Hf) is preferably used as the oxide semiconductor 660.

Note that the oxide semiconductor 660 is not limited to the oxide containing indium. The oxide semiconductor 660 may be, for example, a Zn—Sn oxide or a Ga—Sn oxide.

In the case where the oxide semiconductor 660 is an In-M-Zn oxide (M is Ti, Ga, Y, Zr, La, Ce, Nd, Sn, or Hf) formed by sputtering, it is preferred that the atomic ratio of metal elements of a target used for forming a film of the In-M-Zn oxide satisfy In≥M and Zn≥M. As the atomic ratio of metal elements of such a target, In:M:Zn 1:1:1, In:M:Zn=1:1:1.2, In:M:Zn=3:1:2, and In:M:Zn=2:1:3 are preferable. Note that the atomic ratios of metal elements in the oxide semiconductor 660 vary from those in the sputtering target within an error range of ±40%.

Figure 10A:
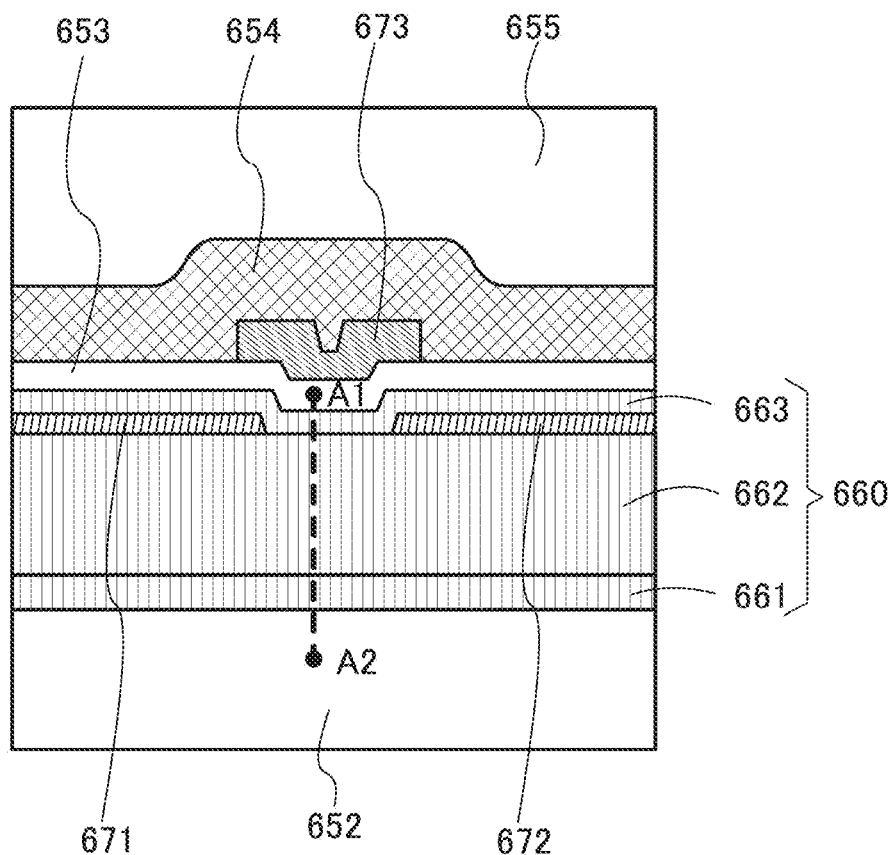
FIGS. 10A and 10B are a cross-sectional view of a transistor and its energy band diagram, respectively, included in one embodiment of the present invention.
Figure 10B:
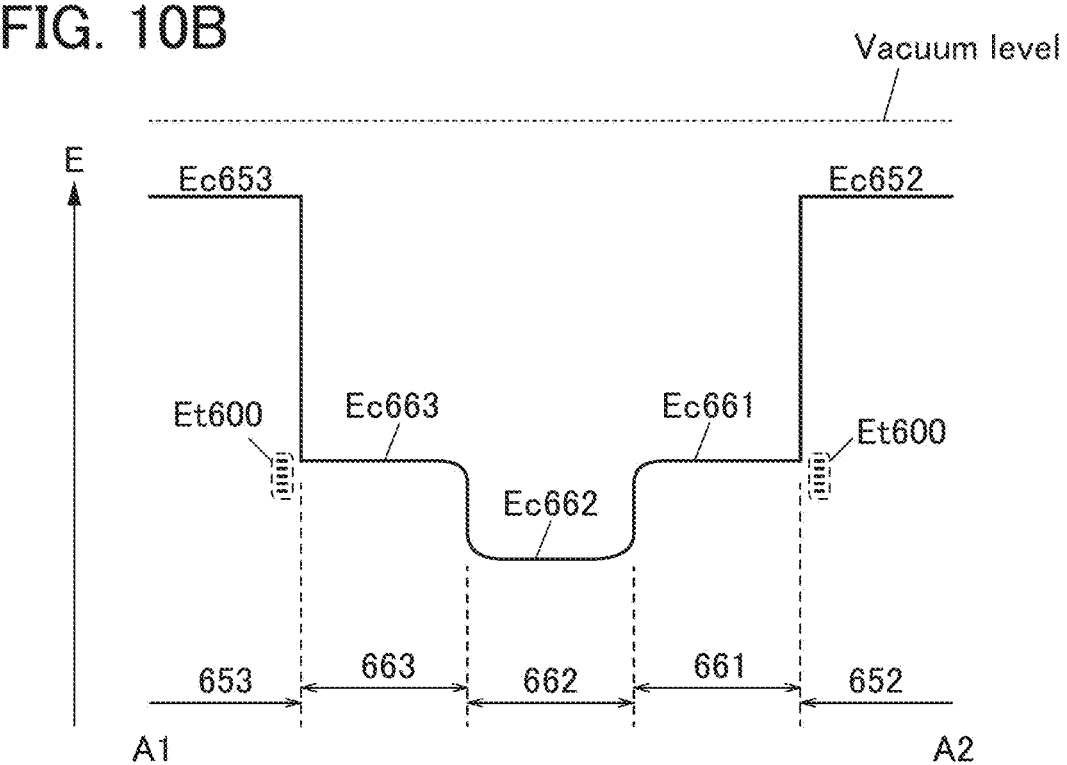

Next, a function and an effect of the oxide semiconductor 660 in which the oxide semiconductor 661, the oxide semiconductor 662, and the oxide semiconductor 663 are stacked will be described using an energy band diagram in FIG. 10B. FIG. 10A is an enlarged view of the channel region of the transistor 600 illustrated in FIG. 9B. FIG. 10B shows an energy band diagram of a portion along the chain line A1-A2 in FIG. 10A. Thus, FIG. 10B illustrates the energy band structure of a channel region of the transistor 600.

In FIG. 10B, Ec652, Ec661, Ec662, Ec663, and Ec653 indicate the energy at the bottom of the conduction band of the insulating film 652, the oxide semiconductor 661, the oxide semiconductor 662, the oxide semiconductor 663, and the gate insulating film 653, respectively.

Here, a difference in energy between the vacuum level and the bottom of the conduction band (the difference is also referred to as "electron affinity") corresponds to a value obtained by subtracting an energy gap from a difference in energy between the vacuum level and the top of the valence band (the difference is also referred to as an ionization potential). Note that the energy gap can be measured using a spectroscopic ellipsometer (UT-300 manufactured by HORIBA JOBIN YVON S.A.S.). The energy difference between the vacuum level and the top of the valence band can be measured using an ultraviolet photoelectron spectroscopy (UPS) device (VersaProbe manufactured by ULVAC-PHI, Inc.).

Note that an In—Ga—Zn oxide that is formed using a sputtering target having an atomic ratio of In:Ga:Zn=1:3:2 has an energy gap of approximately 3.5 eV and an electron affinity of approximately 4.5 eV. An In—Ga—Zn oxide that is formed using a sputtering target having an atomic ratio of In:Ga:Zn=1:3:4 has an energy gap of approximately 3.4 eV and an electron affinity of approximately 4.5 eV. An In—Ga—Zn oxide that is formed using a sputtering target having an atomic ratio of In:Ga:Zn=1:3:6 has an energy gap of approximately 3.3 eV and an electron affinity of approximately 4.5 eV. An In—Ga—Zn oxide that is formed using a sputtering target having an atomic ratio of In:Ga:Zn=1:6:2 has an energy gap of approximately 3.9 eV and an electron affinity of approximately 4.3 eV. An In—Ga—Zn oxide that is formed using a sputtering target having an atomic ratio of In:Ga:Zn=1:6:8 has an energy gap of approximately 3.5 eV and an electron affinity of approximately 4.4 eV. An In—Ga—Zn oxide that is formed using a sputtering target having an atomic ratio of In:Ga:Zn=1:6:10 has an energy gap of approximately 3.5 eV and an electron affinity of approximately 4.5 eV. An In—Ga—Zn oxide that is formed using a sputtering target having an atomic ratio of In:Ga:Zn=1:1:1 has an energy gap of approximately 3.2 eV and an electron affinity of approximately 4.7 eV. An In—Ga—Zn oxide that is formed using a sputtering target having an atomic ratio of In:Ga:Zn=3:1:2 has an energy gap of approximately 2.8 eV and an electron affinity of approximately 5.0 eV.

Since the insulating film 652 and the gate insulating film 653 are insulators, Ec652 and Ec653 are closer to the vacuum level than Ec661, Ec662, and Ec663 (i.e., the insulating film 652 and the gate insulating film 653 have a smaller electron affinity than the oxide semiconductor 661, the oxide semiconductor 662, and the oxide semiconductor 663).

Ec661 is closer to the vacuum level than Ec662. Specifically, Ec661 is preferably located closer to the vacuum level than Ec662 by 0.05 eV or more, 0.07 eV or more, 0.1 eV or more, or 0.15 eV or more and 2 eV or less, 1 eV or less, 0.5 eV or less, or 0.4 eV or less.

Ec663 is closer to the vacuum level than Ec662. Specifically, Ec663 is preferably located closer to the vacuum level than Ec662 by 0.05 eV or more, 0.07 eV or more, 0.1 eV or more, or 0.15 eV or more and 2 eV or less, 1 eV or less, 0.5 eV or less, or 0.4 eV or less.

Mixed regions are formed in the vicinity of the interface between the oxide semiconductor 661 and the oxide semiconductor 662 and the interface between the oxide semiconductor 662 and the oxide semiconductor 663; thus, the energy at the bottom of the conduction band changes continuously. In other words, no state or few states exist at these interfaces.

Accordingly, electrons transfer mainly through the oxide semiconductor 662 in the stacked-layer structure having the above energy band. Therefore, even if an interface state exists at the interface between the oxide semiconductor 661 and the insulating film 652 or the interface between the oxide semiconductor 663 and the gate insulating film 653, the interface state hardly influences the transfer of electrons.

In addition, since no interface state or few interface states exist at the interface between the oxide semiconductor 661 and the oxide semiconductor 662 and the interface between the oxide semiconductor 663 and the oxide semiconductor 662, the transfer of electrons is not interrupted in the region. Consequently, the transistor 600 including the above stacked oxide semiconductors can have high field-effect mobility.

Although trap states Et600 due to impurities or defects might be formed in the vicinity of the interface between the oxide semiconductor 661 and the insulating film 652 and the interface between the oxide semiconductor 663 and the gate insulating film 653 as illustrated in FIG. 10B, the oxide semiconductor 662 can be separated from the trap states owing to the existence of the oxide semiconductor 661 and the oxide semiconductor 663.

In the transistor 600 described in this embodiment, in the channel width direction, the top surface and side surfaces of the oxide semiconductor 662 are in contact with the oxide semiconductor 663, and the bottom surface of the oxide semiconductor 662 is in contact with the oxide semiconductor 661 (see FIG. 9C). Surrounding the oxide semiconductor 662 by the semiconductor 661 and the oxide semiconductor 663 in this manner can further reduce the influence of the trap states.

However, when the energy difference between Ec662 and Ec661 or Ec663 is small, an electron in the oxide semiconductor 662 might reach the trap state by passing over the energy difference. Since the electron is trapped at the trap state, a negative fixed charge is generated at the interface with the insulating film, causing the threshold voltage of the transistor to be shifted in the positive direction.

Therefore, each of the energy gaps between Ec661 and Ec662 and between Ec662 and Ec663 is preferably 0.1 eV or more, further preferably 0.15 eV or more, in which case a change in the threshold voltage of the transistor can be reduced and the transistor can have favorable electrical characteristics.

The band gap of each of the oxide semiconductor 661 and the oxide semiconductor 663 is preferably wider than that of the oxide semiconductor 662.

For the oxide semiconductor 661 and the oxide semiconductor 663, a material containing Al, Ti, Ga, Ge, Y, Zr, Sn, La, Ce, or Hf with a higher atomic ratio than that used for the oxide semiconductor 662 can be used, for example. Specifically, any of the above metal elements in an atomic ratio 1.5 times or more, preferably 2 times or more, further preferably 3 times or more as much as a metal element of the oxide semiconductor 662 is contained. Any of the above metal elements is strongly bonded to oxygen and thus has a function of preventing generation of oxygen vacancy in the oxide semiconductor. That is, an oxygen vacancy is less likely to be generated in the oxide semiconductor 661 and the oxide semiconductor 663 than in the oxide semiconductor 662.

When each of the oxide semiconductor 661, the oxide semiconductor 662, and the oxide semiconductor 663 is an In-M-Zn oxide containing at least indium, zinc, and M (M is a metal such as Al, Ti, Ga, Ge, Y, Zr, Sn, La, Ce, or Hf) and the atomic ratio of In to M and Zn of the oxide semiconductor 661 is $x_1:y_1:z_1$, that of the oxide semiconductor 662 is $x_2:y_2:z_2$, and that of the oxide semiconductor 663 is $x_3:y_3:z_3$, each of $y_1/x_1$ and $y_3/x_3$ is preferably larger than $y_2/x_2$. Each of $y_1/x_1$ and $y_3/x_3$ is one and a half times or more as large as $y_2/x_2$, preferably twice or more as large as $y_2/x_2$, more preferably three times or more as large as $y_2/x_2$. In this case, the transistor can have stable electrical characteristics when $y_2$ is greater than or equal to $x_2$ in the oxide semiconductor 662. However, when $y_2$ is three times or more as large as $x_2$, the field-effect mobility of the transistor is reduced; accordingly, $y_2$ is preferably smaller than three times $x_2$.

In the case where Zn and O are not taken into consideration, the proportion of In and the proportion of M in the oxide semiconductor 661 and the oxide semiconductor 663 are preferably less than 50 atomic % and greater than or equal to 50 atomic %, respectively, and further preferably less than 25 atomic % and greater than or equal to 75 atomic %, respectively. In the case where Zn and O are not taken into consideration, the proportion of In and the proportion of M in the oxide semiconductor 662 are preferably greater than or equal to 25 atomic % and less than 75 atomic %, respectively, and further preferably greater than or equal to 34 atomic % and less than 66 atomic %, respectively.

The thickness of each of the oxide semiconductor 661 and the oxide semiconductor 663 is greater than or equal to 3 nm and less than or equal to 100 nm, preferably greater than or equal to 3 nm and less than or equal to 50 nm. The thickness of the oxide semiconductor 662 is greater than or equal to 3 nm and less than or equal to 200 nm, preferably greater than or equal to 3 nm and less than or equal to 100 nm, further preferably greater than or equal to 3 nm and less than or equal to 50 nm. The oxide semiconductor 662 is preferably thicker than the oxide semiconductor 661 and the oxide semiconductor 663.

Note that stable electrical characteristics can be effectively imparted to a transistor in which an oxide semiconductor serves as a channel by reducing the concentration of impurities in the oxide semiconductor to make the oxide semiconductor intrinsic or substantially intrinsic. The term "substantially intrinsic" refers to the state where an oxide semiconductor has a carrier density lower than $1\times10^{17}/cm^3$, preferably lower than $1\times10^{15}/cm^3$, further preferably lower than $1\times10^{13}/cm^3$.

In the oxide semiconductor, hydrogen, nitrogen, carbon, silicon, and a metal element other than a main component are impurities. For example, hydrogen and nitrogen form donor levels to increase the carrier density, and silicon forms impurity levels in the oxide semiconductor. The impurity level becomes a trap, which might deteriorate the electric characteristics of the transistor. Therefore, it is preferable to reduce the concentration of the impurities in the oxide semiconductors 661, 662, and 663 and at interfaces between the oxide semiconductors.

In order to make the oxide semiconductor intrinsic or substantially intrinsic, for example, the concentration of silicon at a certain depth of the oxide semiconductor or in a certain region of the oxide semiconductor, which is measured by SIMS, is lower than $1\times10^{19}$ atoms/cm$^3$, preferably lower than $5\times10^{18}$ atoms/cm$^3$, further preferably lower than $1\times10^{18}$ atoms/cm$^3$. The concentration of hydrogen at a certain depth of the oxide semiconductor or in a certain region of the oxide semiconductor is lower than or equal to $2\times10^{20}$ atoms/cm$^3$, preferably lower than or equal to $5\times10^{19}$ atoms/cm$^3$, further preferably lower than or equal to $1\times10^{19}$ atoms/cm$^3$, still further preferably lower than or equal to $5\times10^{18}$ atoms/cm$^3$. The concentration of nitrogen at a certain depth of the oxide semiconductor or in a certain region of the oxide semiconductor is lower than $5\times10^{19}$ atoms/cm$^3$, preferably lower than or equal to $5\times10^{18}$ atoms/cm$^3$, further preferably lower than or equal to $1\times10^{18}$ atoms/cm$^3$, still further preferably lower than or equal to $5\times10^{17}$ atoms/cm$^3$.

In addition, in the case where the oxide semiconductor includes a crystal, the crystallinity of the oxide semiconductor might be decreased if silicon or carbon is included at high concentration. In order not to lower the crystallinity of the oxide semiconductor, for example, the concentration of silicon at a certain depth of the oxide semiconductor or in a certain region of the oxide semiconductor is lower than $1\times10^{19}$ atoms/cm$^3$, preferably lower than $5\times10^{18}$ atoms/cm$^3$, further preferably lower than $1\times10^{18}$ atoms/cm$^3$. Furthermore, the concentration of carbon at a certain depth of the oxide semiconductor or in a certain region of the oxide semiconductor is lower than $1\times10^{19}$ atoms/cm$^3$, preferably lower than $5\times10^{18}$ atoms/cm$^3$, further preferably lower than $1\times10^{18}$ atoms/cm$^3$, for example.

A transistor in which a highly purified oxide semiconductor is used for a channel region as described above has an extremely low off-state current. In the case where the voltage between a source and a drain is set at approximately 0.1 V, 5 V, or 10 V, for example, the off-state current standardized on the channel width of the transistor can be as low as several yoctoamperes per micrometer to several zeptoamperes per micrometer.

In the transistor 600 described in this embodiment, the gate electrode 673 is formed to electrically surround the oxide semiconductor 660 in the channel width direction; consequently, a gate electric field is applied to the semiconductor 660 in the side surface direction in addition to the perpendicular direction (see FIG. 9C). In other words, a gate electric field is applied to the whole oxide semiconductor, so that current flows through the entire oxide semiconductor 662 serving as a channel, leading to a further increase in on-state current.

<Crystal Structure of Oxide Semiconductor>

Next, a structure of an oxide semiconductor film is described below.

In this specification, the term "parallel" indicates that the angle formed between two straight lines is greater than or equal to −10° and less than or equal to 10°, and accordingly also includes the case where the angle is greater than or equal to −5° and less than or equal to 5°. The term "substantially parallel" indicates that the angle formed between two straight lines is greater than or equal to −30° and less than or equal to 30°. In addition, the term "perpendicular" indicates that the angle formed between two straight lines is greater than or equal to 80° and less than or equal to 100° and accordingly also includes the case where the angle is greater than or equal to 85° and less than or equal to 95°. The term "substantially perpendicular" indicates that the angle formed between two straight lines is greater than or equal to 60° and less than or equal to 120°.

In this specification, trigonal and rhombohedral crystal systems are included in a hexagonal crystal system.

An oxide semiconductor film is classified into a non-single-crystal oxide semiconductor film and a single crystal oxide semiconductor film. Alternatively, an oxide semiconductor is classified into, for example, a crystalline oxide semiconductor and an amorphous oxide semiconductor.

Examples of a non-single-crystal oxide semiconductor include a c-axis aligned crystalline oxide semiconductor (CAAC-OS), a polycrystalline oxide semiconductor, a microcrystalline oxide semiconductor, and an amorphous oxide semiconductor. In addition, examples of a crystalline oxide semiconductor include a single crystal oxide semiconductor, a CAAC-OS, a polycrystalline oxide semiconductor, and a microcrystalline oxide semiconductor.

First, a CAAC-OS film will be described.

The CAAC-OS film is one of oxide semiconductor films having a plurality of c-axis aligned crystal parts.

With a transmission electron microscope (TEM), a combined analysis image (also referred to as a high-resolution TEM image) of a bright-field image and a diffraction pattern of the CAAC-OS film is observed. Consequently, a plurality of crystal parts are observed. However, in the high-resolution TEM image, a boundary between crystal parts, that is, a grain boundary is not clearly observed. Thus, in the CAAC-OS film, a reduction in electron mobility due to the grain boundary is less likely to occur.

According to the high-resolution cross-sectional TEM image of the CAAC-OS film observed in a direction substantially parallel to a sample surface, metal atoms are arranged in a layered manner in the crystal parts. Each metal atom layer has a form that reflects unevenness of a surface over which the CAAC-OS film is formed (hereinafter, a surface over which the CAAC-OS film is formed is referred to as a formation surface) or a top surface of the CAAC-OS film, and is arranged parallel to the formation surface or the top surface of the CAAC-OS film.

On the other hand, according to the high-resolution plan-view TEM image of the CAAC-OS film observed in a direction substantially perpendicular to the sample surface, metal atoms are arranged in a triangular or hexagonal configuration in the crystal parts. However, there is no regularity of arrangement of metal atoms between different crystal parts.

A CAAC-OS film is subjected to structural analysis with an X-ray diffraction (XRD) apparatus. For example, when the CAAC-OS film including an InGaZnO$_4$ crystal is analyzed by an out-of-plane method, a peak appears frequently when the diffraction angle (2 θ) is around 31°. This peak is derived from the (009) plane of the InGaZnO$_4$ crystal, which indicates that crystals in the CAAC-OS film have c-axis alignment, and that the c-axes are aligned in a direction substantially perpendicular to the formation surface or the top surface of the CAAC-OS film.

Note that when the CAAC-OS film with an InGaZnO$_4$ crystal is analyzed by an out-of-plane method, a peak of 2θ may also be observed at around 36°, in addition to the peak of 2θ at around 31°. The peak of 2θ at around 36° indicates that a crystal having no c-axis alignment is included in part of the CAAC-OS film. It is preferable that in the CAAC-OS film, a peak of 2θ appear at around 31° and a peak of 2θ not appear at around 36°.

The CAAC-OS film is an oxide semiconductor film having low impurity concentration. The impurity is an element other than the main components of the oxide semiconductor film, such as hydrogen, carbon, silicon, or a transition metal element. In particular, an element that has higher bonding strength to oxygen than a metal element included in the oxide semiconductor film, such as silicon, disturbs the atomic arrangement of the oxide semiconductor film by depriving the oxide semiconductor film of oxygen and causes a decrease in crystallinity. Furthermore, a heavy metal such as iron or nickel, argon, carbon dioxide, or the like has a large atomic radius (or molecular radius), and thus disturbs the atomic arrangement of the oxide semiconductor film and causes a decrease in crystallinity when it is contained in the oxide semiconductor film. Note that the impurity contained in the oxide semiconductor film might serve as a carrier trap or a carrier generation source.

The CAAC-OS film is an oxide semiconductor film having a low density of defect states. In some cases, oxygen vacancies in the oxide semiconductor film serve as carrier traps or serve as carrier generation sources when hydrogen is captured therein.

The state in which impurity concentration is low and density of defect states is low (the number of oxygen vacancies is small) is referred to as a "highly purified intrinsic" or "substantially highly purified intrinsic" state. A highly purified intrinsic or substantially highly purified intrinsic oxide semiconductor film has few carrier generation sources, and thus can have a low carrier density. Thus, a transistor including the oxide semiconductor film rarely has negative threshold voltage (is rarely normally on). The highly purified intrinsic or substantially highly purified intrinsic oxide semiconductor film has few carrier traps. Accordingly, the transistor including the oxide semiconductor film has little variation in electrical characteristics and high reliability. Electric charge trapped by the carrier traps in the oxide semiconductor film takes a long time to be released, and might behave like fixed electric charge. Thus, the transistor which includes the oxide semiconductor film having high impurity concentration and a high density of defect states has unstable electrical characteristics in some cases.

With the use of the CAAC-OS film in a transistor, variation in the electrical characteristics of the transistor due to irradiation with visible light or ultraviolet light is small.

Next, a microcrystalline oxide semiconductor film will be described.

A microcrystalline oxide semiconductor film has a region where a crystal part is observed in a high resolution TEM image and a region where a crystal part is not clearly observed in a high resolution TEM image. In most cases, a crystal part in the microcrystalline oxide semiconductor is greater than or equal to 1 nm and less than or equal to 100 nm, or greater than or equal to 1 nm and less than or equal to 10 nm. A microcrystal with a size greater than or equal to 1 nm and less than or equal to 10 nm, or a size greater than or equal to 1 nm and less than or equal to 3 nm is specifically referred to as nanocrystal (nc). An oxide semiconductor film including nanocrystal is referred to as an nc-OS (nanocrystalline oxide semiconductor) film. In a high resolution TEM image of the nc-OS film, for example, a grain boundary cannot be found clearly in the nc-OS film sometimes.

In the nc-OS film, a microscopic region (for example, a region with a size greater than or equal to 1 nm and less than or equal to 10 nm, in particular, a region with a size greater than or equal to 1 nm and less than or equal to 3 nm) has a periodic atomic order. There is no regularity of crystal orientation between different crystal parts in the nc-OS film. Thus, the orientation of the whole film is not observed. Accordingly, in some cases, the nc-OS film cannot be distinguished from an amorphous oxide semiconductor film depending on an analysis method. For example, when the nc-OS film is subjected to structural analysis by an out-of-plane method with an XRD apparatus using an X-ray having a diameter larger than that of a crystal part, a peak which shows a crystal plane does not appear. Furthermore, a diffraction pattern like a halo pattern appears in a selected-area electron diffraction pattern of the nc-OS film which is obtained by using an electron beam having a probe diameter (e.g., larger than or equal to 50 nm) larger than the diameter of a crystal part. Meanwhile, spots are shown in a nanobeam electron diffraction pattern of the nc-OS film obtained by using an electron beam having a probe diameter close to, or smaller than the diameter of a crystal part. Furthermore, in a nanobeam electron diffraction pattern of the nc-OS film, regions with high luminance in a circular (ring) pattern are shown in some cases. Also in a nanobeam electron diffraction pattern of the nc-OS film, a plurality of spots is shown in a ring-like region in some cases.

The nc-OS film is an oxide semiconductor film that has high regularity as compared to an amorphous oxide semiconductor film. Therefore, the nc-OS film has a lower density of defect states than an amorphous oxide semiconductor film. However, there is no regularity of crystal orientation between different crystal parts in the nc-OS film; hence, the nc-OS film has a higher density of defect states than the CAAC-OS film.

Next, an amorphous oxide semiconductor film will be described.

The amorphous oxide semiconductor film has disordered atomic arrangement and no crystal part. For example, the amorphous oxide semiconductor film does not have a specific state as in quartz.

In the high-resolution TEM image of the amorphous oxide semiconductor film, crystal parts cannot be found.

When the amorphous oxide semiconductor film is subjected to structural analysis by an out-of-plane method with an XRD apparatus, a peak which shows a crystal plane does not appear. A halo pattern is shown in an electron diffraction pattern of the amorphous oxide semiconductor film. Furthermore, a halo pattern is shown but a spot is not shown in a nanobeam electron diffraction pattern of the amorphous oxide semiconductor film.

Note that an oxide semiconductor film may have a structure having physical properties between the nc-OS film and the amorphous oxide semiconductor film. The oxide semiconductor film having such a structure is specifically referred to as an amorphous-like oxide semiconductor (a-like OS) film.

In a high-resolution TEM image of the a-like OS film, a void may be seen. Furthermore, in the high-resolution TEM image, there are a region where a crystal part is clearly observed and a region where a crystal part is not observed. In the a-like OS film, crystallization by a slight amount of electron beam used for TEM observation occurs and growth of the crystal part is found sometimes. In contrast, crystallization by a slight amount of electron beam used for TEM observation is hardly observed in the nc-OS film having good quality.

Note that the crystal part size in the a-like OS film and the nc-OS film can be measured using high-resolution TEM images. For example, an $InGaZnO_4$ crystal has a layered structure in which two Ga—Zn—O layers are included between In—O layers. A unit cell of the $InGaZnO_4$ crystal has a structure in which nine layers, including three In—O layers and six Ga—Zn—O layers, are layered in the c-axis direction. Accordingly, the spacing between these adjacent layers is equivalent to the lattice spacing on the (009) plane (also referred to as d value). The value is calculated to be 0.29 nm from crystal structure analysis. Thus, focusing on lattice fringes in the high-resolution TEM image, each of lattice fringes in which the lattice spacing therebetween is greater than or equal to 0.28 nm and less than or equal to 0.30 nm corresponds to the a-b plane of the $InGaZnO_4$ crystal.

The density of an oxide semiconductor film might vary depending on its structure. For example, if the composition of an oxide semiconductor film is determined, the structure of the oxide semiconductor film can be estimated from a comparison between the density of the oxide semiconductor film and the density of a single crystal oxide semiconductor film having the same composition as the oxide semiconductor film. For example, the density of the a-like OS film is higher than or equal to 78.6% and lower than 92.3% of the density of the single crystal oxide semiconductor having the same composition. For example, the density of each of the nc-OS film and the CAAC-OS film is higher than or equal to 92.3% and lower than 100% of the density of the single crystal oxide semiconductor having the same composition.

Note that it is difficult to deposit an oxide semiconductor film whose density is lower than 78% of the density of the single crystal oxide semiconductor film.

Specific examples of the above description will be given. For example, in the case of an oxide semiconductor film with an atomic ratio of In:Ga:Zn=1:1:1, the density of single-crystal InGaZnO$_4$ with a rhombohedral crystal structure is 6.357 g/cm$^3$. Thus, for example, in the case of the oxide semiconductor film with an atomic ratio of In:Ga:Zn=1:1:1, the density of an a-like OS film is higher than or equal to 5.0 g/cm$^3$ and lower than 5.9 g/cm$^3$. In addition, for example, in the case of the oxide semiconductor film with an atomic ratio of In:Ga:Zn=1:1:1, the density of an nc-OS film or a CAAC-OS film is higher than or equal to 5.9 g/cm$^3$ and lower than 6.3 g/cm$^3$.

Note that single crystals with the same composition do not exist in some cases. In such a case, by combining single crystals with different compositions at a given proportion, it is possible to calculate density that corresponds to the density of a single crystal with a desired composition. The density of the single crystal with a desired composition may be calculated using weighted average with respect to the combination ratio of the single crystals with different compositions. Note that it is preferable to combine as few kinds of single crystals as possible for density calculation.

Note that an oxide semiconductor film may be a stacked film including two or more films of an amorphous oxide semiconductor film, an a-like OS film, a microcrystalline oxide semiconductor film, and a CAAC-OS film, for example.

For the deposition of the CAAC-OS film by a sputtering method, the following conditions are preferably used.

By reducing the amount of impurities entering the CAAC-OS film during the deposition, the crystal state can be prevented from being broken by the impurities. For example, the concentration of impurities (e.g., hydrogen, water, carbon dioxide, and nitrogen) that exist in the treatment chamber may be reduced. Furthermore, the concentration of impurities in a deposition gas may be reduced. Specifically, a deposition gas whose dew point is −80° C. or lower, preferably −100° C. or lower is used.

By increasing the substrate heating temperature during the deposition, migration of a sputtered particle is likely to occur after the sputtered particle reaches a substrate surface. Specifically, the substrate heating temperature during the deposition is higher than or equal to 100° C. and lower than or equal to 740° C., preferably higher than or equal to 200° C. and lower than or equal to 500° C. By increasing the substrate heating temperature during the deposition, when the flat-plate-like or pellet-like sputtered particle reaches the substrate, migration occurs on the substrate, so that a flat plane of the sputtered particle is attached to the substrate.

Furthermore, it is preferable that the proportion of oxygen in the deposition gas be increased and the power be optimized in order to reduce plasma damage at the deposition. The proportion of oxygen in the deposition gas is higher than or equal to 30 vol %, preferably 100 vol %.

As an example of the target, an In—Ga—Zn-based oxide target will be described below.

The In—Ga—Zn-based oxide target, which is polycrystalline, is made by mixing InO$_X$ powder, GaO$_Y$ powder, and ZnO$_Z$ powder in a predetermined molar ratio, applying pressure, and performing heat treatment at a temperature higher than or equal to 1000° C. and lower than or equal to 1500° C. Note that X, Y, and Z are each a given positive number. Here, the predetermined molar ratio of InO$_X$ powder to GaO$_Y$ powder and ZnO$_Z$ powder is, for example, 2:2:1, 8:4:3, 3:1:1, 1:1:1, 4:2:3, 1:4:4, 3:1:2, or 2:1:3. The kinds of powder and the molar ratio for mixing powder may be determined as appropriate depending on the desired target.

<Gate Electrode>

The gate electrode 673 can be formed using a metal element selected from chromium (Cr), copper (Cu), aluminum (Al), gold (Au), silver (Ag), zinc (Zn), molybdenum (Mo), tantalum (Ta), titanium (Ti), tungsten (W), manganese (Mn), nickel (Ni), iron (Fe), cobalt (Co), and ruthenium (Ru); an alloy containing any of these metal element as its component; an alloy containing a combination of any of these metal elements; or the like. The gate electrode 673 may have a single-layer structure or a stacked-layer structure of two or more layers. For example, any of the following structures can be employed: a single-layer structure of an aluminum film containing silicon; a two-layer structure in which a titanium film is stacked over an aluminum film; a two-layer structure in which a titanium film is stacked over a titanium nitride film; a two-layer structure in which a tungsten film is stacked over a titanium nitride film; a two-layer structure in which a tungsten film is stacked over a tantalum nitride film or a tungsten nitride film; a three-layer structure in which a titanium film, an aluminum film, and a titanium film are stacked in this order; a single-layer structure of a Cu—Mn alloy film; a two-layer structure in which a Cu film is stacked over a Cu—Mn alloy film; and a three-layer structure in which a Cu—Mn alloy film, a Cu film, and a Cu—Mn alloy film are stacked in this order. A Cu—Mn alloy film is preferably used because of its low electrical resistance and because it forms manganese oxide at the interface with an insulating film containing oxygen and manganese oxide can prevent Cu diffusion.

The gate electrode 673 can also be formed using a light-transmitting conductive material such as indium tin oxide, indium oxide containing tungsten oxide, indium zinc oxide containing tungsten oxide, indium oxide containing titanium oxide, indium tin oxide containing titanium oxide, indium zinc oxide, or indium tin oxide to which silicon oxide is added. It is also possible to have a layered structure formed using the above light-transmitting conductive material and the above metal element.

<Gate Insulating Film>

The gate insulating film 653 can be formed using an insulating film containing at least one of aluminum oxide, magnesium oxide, silicon oxide, silicon oxynitride, silicon nitride oxide, silicon nitride, gallium oxide, germanium oxide, yttrium oxide, zirconium oxide, lanthanum oxide, neodymium oxide, hafnium oxide, and tantalum oxide. The gate insulating film 653 may be a stack including any of the above materials. The gate insulating film 653 may contain lanthanum (La), nitrogen, or zirconium (Zr) as an impurity.

An example of a stacked-layer structure of the gate insulating film 653 will be described. The gate insulating film 653 contains oxygen, nitrogen, silicon, or hafnium, for example. Specifically, the gate insulating film 653 preferably includes hafnium oxide and silicon oxide or silicon oxynitride.

Hafnium oxide has a higher dielectric constant than silicon oxide and silicon oxynitride. Therefore, by using hafnium oxide, a physical thickness can be made larger than an equivalent oxide thickness; thus, even in the case where the equivalent oxide thickness is less than or equal to 10 nm or less than or equal to 5 nm, leakage current due to tunnel current can be small. That is, it is possible to provide a transistor with a low off-state current. Moreover, hafnium oxide with a crystalline structure has higher dielectric constant than hafnium oxide with an amorphous structure. Therefore, it is preferable to use hafnium oxide with a crystalline structure in order to provide a transistor with a low off-state current. Examples of the crystalline structure include a monoclinic crystal structure and a cubic crystal structure. Note that one embodiment of the present invention is not limited to the above examples.

<Source Electrode and Drain Electrode>

The source electrode 671 and the drain electrode 672 can be formed using a material used for the gate electrode 673. A Cu—Mn alloy film is preferably used because of its low electrical resistance and because it forms manganese oxide at the interface with the oxide semiconductor 660 and manganese oxide can prevent Cu diffusion.

<Protective Insulating Film>

The insulating film 654 has a function of blocking oxygen, hydrogen, water, alkali metal, alkaline earth metal, and the like. The provision of the insulating film 654 can prevent outward diffusion of oxygen from the oxide semiconductor 660 and entry of hydrogen, water, or the like into the oxide semiconductor 660 from the outside. The insulating film 654 can be a nitride insulating film, for example. The nitride insulating film is formed using silicon nitride, silicon nitride oxide, aluminum nitride, aluminum nitride oxide, or the like. Note that instead of the nitride insulating film having a blocking effect against oxygen, hydrogen, water, alkali metal, alkaline earth metal, and the like, an oxide insulating film having a blocking effect against oxygen, hydrogen, water, and the like, may be provided. As the oxide insulating film having a blocking effect against oxygen, hydrogen, water, and the like, an aluminum oxide film, an aluminum oxynitride film, a gallium oxide film, a gallium oxynitride film, an yttrium oxide film, an yttrium oxynitride film, a hafnium oxide film, and a hafnium oxynitride film can be given.

An aluminum oxide film is preferably used as the insulating film 654 because it is highly effective in preventing transmission of both oxygen and impurities such as hydrogen and moisture. Thus, during and after the manufacturing process of the transistor, the aluminum oxide film can suitably function as a protective film that has effects of preventing entry of impurities such as hydrogen and moisture, which cause variations in the electrical characteristics of the transistor, into the oxide semiconductor 660, preventing release of oxygen, which is the main component of the oxide semiconductor 660, from the oxide semiconductor, and preventing unnecessary release of oxygen from the insulating film 652. In addition, oxygen contained in the aluminum oxide film can be diffused into the oxide semiconductor.

<Interlayer Insulating Film>

The insulating film 655 is preferably formed over the insulating film 654. The insulating film 655 can be an insulating film containing one or more of magnesium oxide, silicon oxide, silicon oxynitride, silicon nitride oxide, silicon nitride, gallium oxide, germanium oxide, yttrium oxide, zirconium oxide, lanthanum oxide, neodymium oxide, hafnium oxide, and tantalum oxide. The insulating film 655 may be a stack of any of the above materials.

<Second Gate Electrode>

Figure 11A:
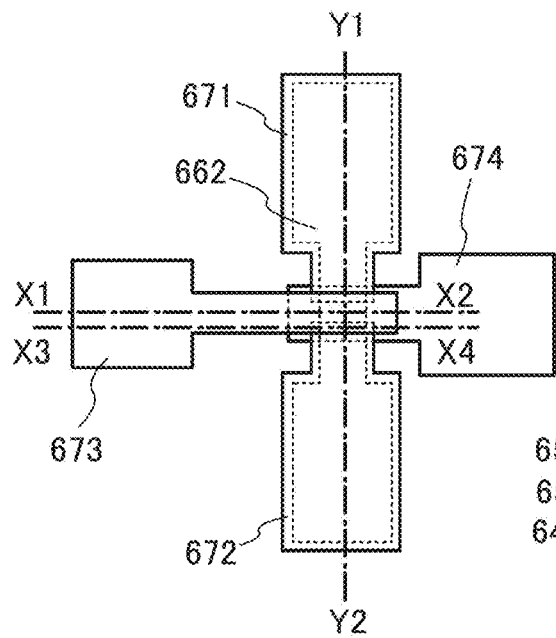
FIG. 11A is a top view and FIGS. 11B to 11D are cross-sectional views of a transistor included in one embodiment of the present invention.
Figure 11B:
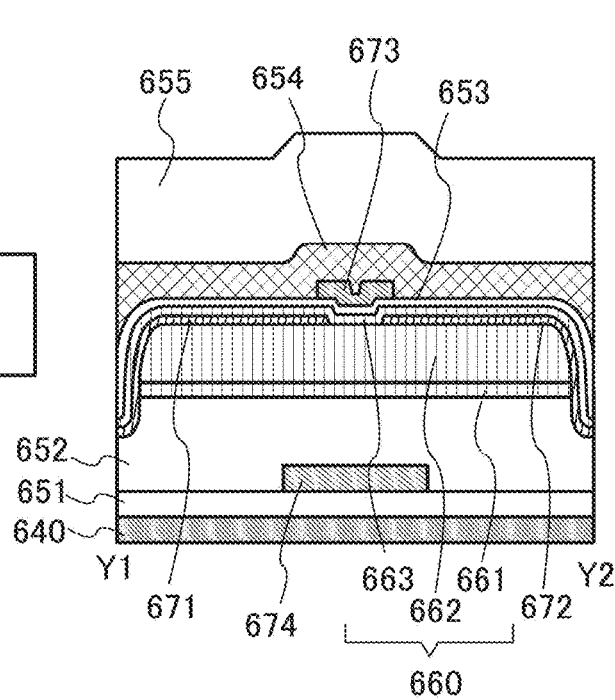
Figure 11C:
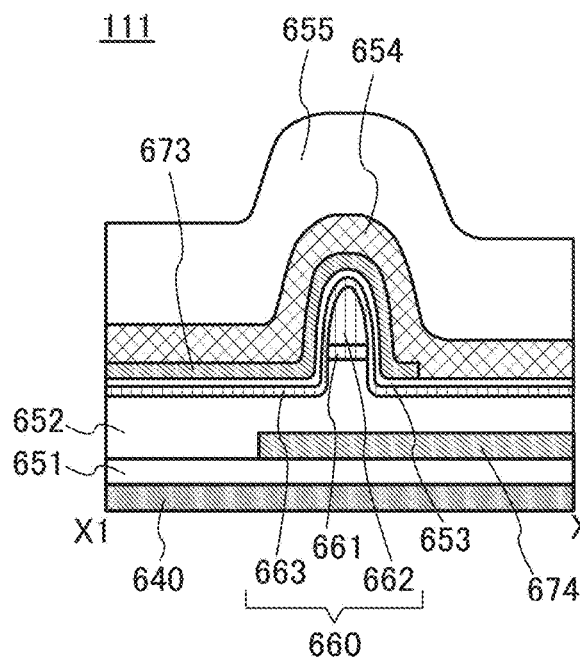
Figure 11D:
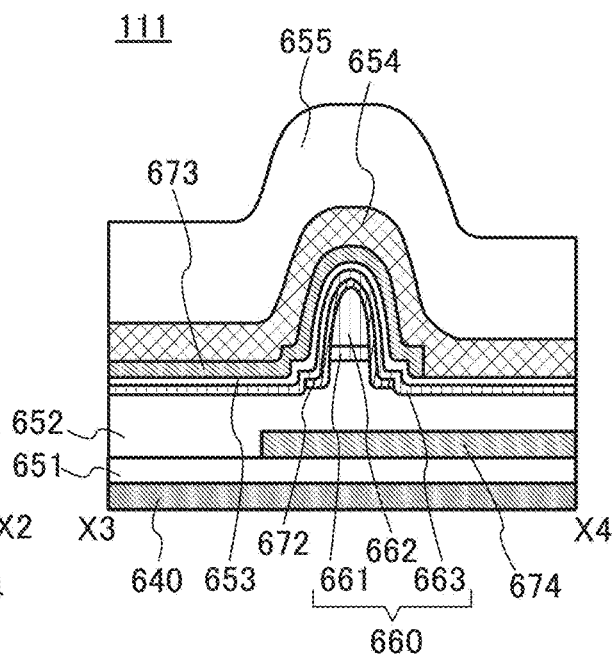

Although an example in which the transistor 600 has a single gate electrode is shown in FIGS. 9A to 9D, one embodiment of the present invention is not limited thereto. The transistor may include a plurality of gate electrodes. An example in which the transistor 600 is provided with a conductive film 674 as a second gate electrode is shown in FIGS. 11A to 11D. FIG. 11A is the top view. FIG. 11B corresponds to a cross section taken along the dashed-dotted line Y1-Y2 in FIG. 11A. FIG. 11C corresponds to a cross section taken along the dashed-dotted line X1-X2 in FIG. 11A. FIG. 11D corresponds to a cross section taken along the dashed-dotted line X3-X4 in FIG. 11A. In FIGS. 11A to 11D, some components are scaled up or down or omitted for easy understanding.

For the composition of the conductive film 674, the description of the gate electrode 673 may be referred to. The conductive film 674 functions as a second gate electrode layer. The same potential as that of the gate electrode 673 or a different potential from that of the gate electrode 673 may be applied to the conductive film 674.

The structure and method described in this embodiment can be implemented by being combined as appropriate with any of the other structures and methods described in the other embodiments.

Embodiment 4

In this embodiment, electronic devices of embodiments of the present invention will be described with reference to FIGS. 12A to 12F.

FIGS. 12A to 12F illustrate electronic devices. These electronic devices can include a housing 5000, a display portion 5001, a speaker 5003, an LED lamp 5004, operation keys 5005 (including a power switch or an operation switch), a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 5008, and the like.

Figure 12A:
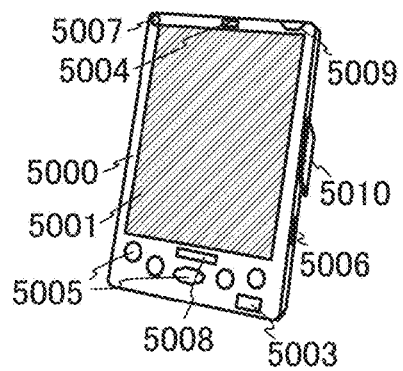
FIGS. 12A to 12F each illustrate an electronic device according to one embodiment of the present invention.
Figure 12B:
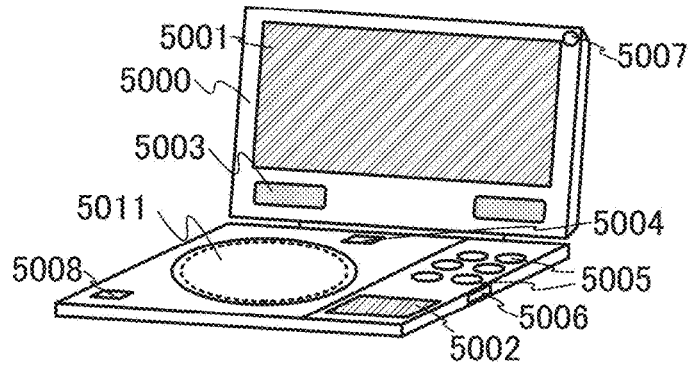
Figure 12C:
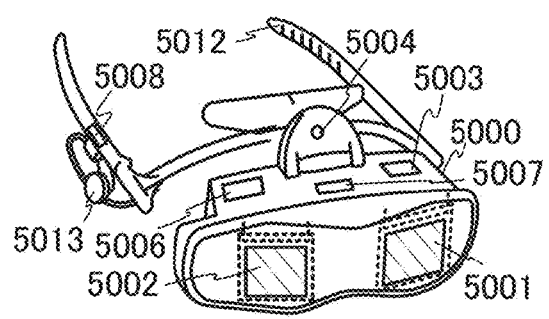
Figure 12D:
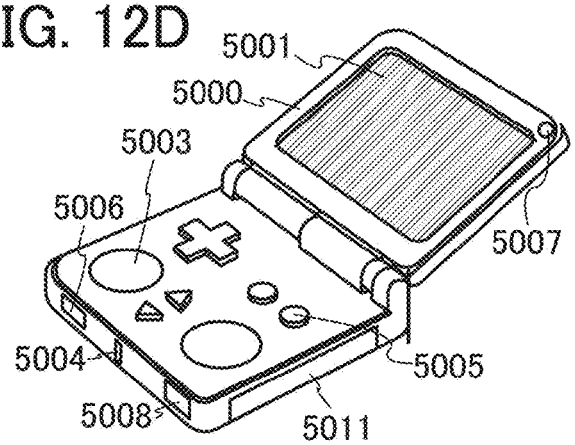
Figure 12E:
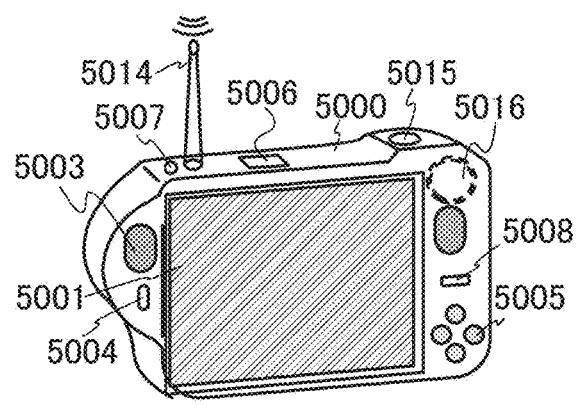
Figure 12F:
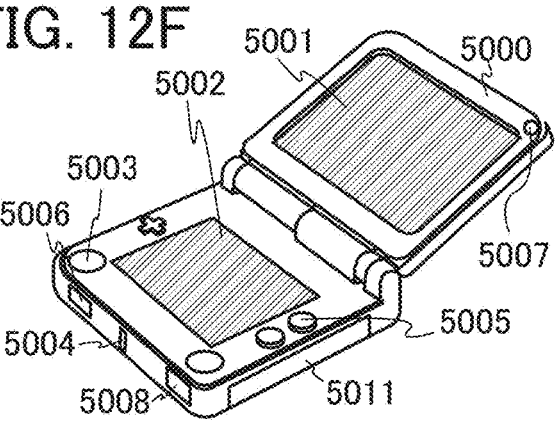

FIG. 12A illustrates a mobile computer, which can include a switch 5009, an infrared port 5010, and the like in addition to the above components. FIG. 12B illustrates a portable image reproducing device (e.g., a DVD player), which is provided with a memory medium and can include a second display portion 5002, a memory medium reading portion 5011, and the like in addition to the above components. FIG. 12C illustrates a goggle-type display, which can include the second display portion 5002, a support 5012, an earphone 5013, and the like in addition to the above components. FIG. 12D illustrates a portable game machine, which can include the memory medium reading portion 5011 and the like in addition to the above components. FIG. 12E illustrates a digital camera, which has a television reception function and can include an antenna 5014, a shutter button 5015, an image receiving portion 5016, and the like in addition to the above components. FIG. 12F illustrates a portable game machine, which can include the second display portion 5002, the memory medium reading portion 5011, and the like in addition to the above components.

The electronic devices illustrated in FIGS. 12A to 12F can have a variety of functions, such as a function of displaying a variety of information (e.g., a still image, a moving image, and a text image) on a display portion, a touch panel function, a function of displaying a calendar, date, time, and the like, a function of controlling processing with a variety of software (programs), a wireless communication function, a function of being connected to a variety of computer networks with a wireless communication function, a function of transmitting and receiving a variety of data with a wireless communication function, and a function of reading a program or data stored in a recording medium and displaying the program or data on a display portion.

Furthermore, the electronic device including a plurality of display portions can have a function of displaying image information mainly on one display portion while displaying text information on another display portion, a function of displaying a three-dimensional image by displaying images where parallax is utilized on a plurality of display portions, or the like. Furthermore, the electronic device including an image receiving portion can have a function of photographing a still image, a function of photographing a moving image, a function of automatically or manually correcting a photographed image, a function of storing a photographed image in a memory medium (an external memory medium or a memory medium incorporated in the camera), a function of displaying a photographed image on the display portion, or the like. Note that functions that can be provided for the electronic devices illustrated in FIGS. 12A to 12F are not limited thereto, and the electronic devices can have a variety of functions.

Each of the electronic devices described in this embodiment incorporates a plurality of batteries and has a wireless receiving portion capable of wireless charging.

Figure 13A:
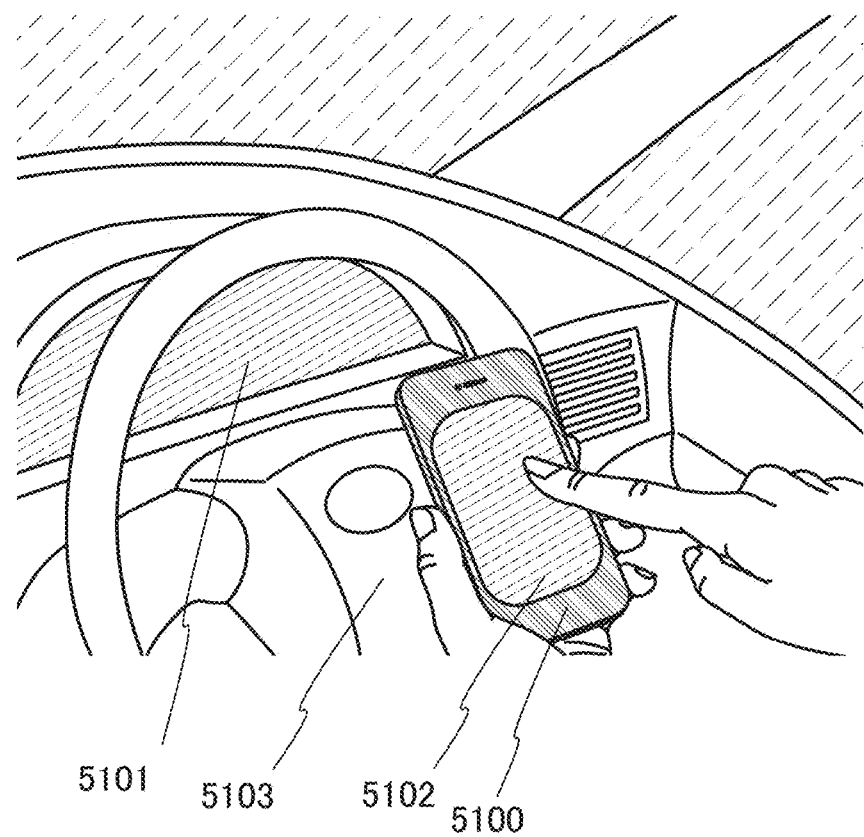
FIGS. 13A and 13B each illustrate an electronic device according to one embodiment of the present invention.
Figure 13B:
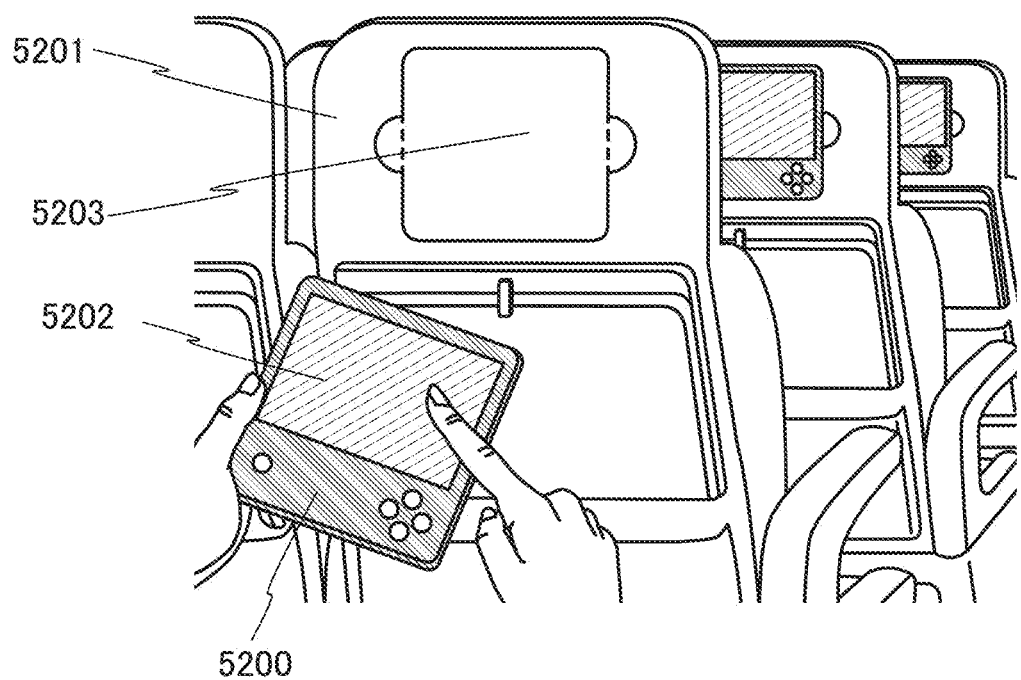

Usage examples of electronic devices are illustrated in FIGS. 13A and 13B.

FIG. 13A shows an example where an information terminal is operated in a moving object such as a car.

The numeral 5103 indicates a steering wheel, which includes an antenna inside. The antenna in the steering wheel 5103 can supply electric power to an electronic device 5100. The electronic device 5100 has a plurality of batteries, and at least one of the batteries is charged by wireless charging. The steering wheel 5103 may be provided with a jig that can fix the electronic device 5100. If the electronic device 5100 is fixed on the steering wheel 5103, the user can make a phone call or a video-phone call without using his/her hands. Furthermore, through voice authentication with the use of a microphone provided in the electronic device 5100, the car can be driven by a voice of the driver.

For example, by operating the electronic device 5100 while the car is parked, the positional information can be displayed on a display portion 5102. Furthermore, information not displayed on a display portion 5101 of the car, such as engine speed, steering wheel angle, temperature, and tire pressure may be displayed on the display portion 5102. The display portion 5102 has a touch input function. Furthermore, one or more cameras to image the outside of the car can be used to display the outside image on the display portion 5102. That is, the display portion 5102 can be used as a back monitor, for example. Furthermore, for preventing drowsy driving, the electronic device 5100 may operate as follows, for example: while wirelessly receiving information such as the driving speed from the car to monitor the driving speed, the electronic device 5100 images the driver at the time of driving and when a period for which the driver closes his/her eyes is long, it vibrates, beeps, or plays music (depending on the setting that can be selected by the driver as appropriate). Furthermore, by stopping imaging the driver while the car is parked, power consumption can be reduced. In addition, the batteries of the electronic device 5100 may be wirelessly charged while the car is parked.

The electronic device 5100 is expected to be used in a variety of ways in a moving object such as a car, as described above, and is desired to incorporate a number of sensors and a plurality of antennas that enable various functions thereof. Although a moving object such as a car has a power supply, the power supply is limited. In view of the electric power to drive the moving object, it is preferable that the electric power used for the electronic device 5100 be as low as possible. For an electric vehicle, in particular, power consumed by the electronic device 5100 may decrease the travel distance. Even if the electronic device 5100 has a variety of functions, it is not often that all the functions are used at a time, and only one or two functions are usually used as necessary. In the case where the electronic device 5100 including a plurality of batteries, each of which is prepared for a different function, has a variety of functions, only the function to be used is turned on and electric power is supplied thereto from a battery corresponding to that function; whereby, power consumption can be reduced. Furthermore, batteries corresponding to the functions not in use, among the plurality of batteries, can be wirelessly charged from an antenna provided in the car.

FIG. 13B illustrates an example in which an information terminal is operated in an airplane or the like. Since a period in which an individual can use his/her own information terminal is limited in an airplane or the like, the airplane is desired to be equipped with information terminals that the passengers can use when the flight is long.

An electronic device 5200, having a display portion 5202 that displays images such as a movie, a game, and a commercial, is an information terminal with which the current flying location and the remaining flight time can be obtained in real time, owing to its communication function. The display portion 5202 has a touch input function.

The electronic device 5200 can be fit into a depressed portion in a seat 5201, and an antenna installation portion 5203 is provided in a position that overlaps with the electronic device 5200, whereby the electronic device 5200 can be wirelessly charged while it is fit into the depressed portion. Furthermore, the electronic device 5200 can function as a telephone or communication tool when the user is sick and wants to contact a flight attendant, for example. If the electronic device 5200 has a translation function, the user can communicate with a flight attendant by using the display portion 5202 of the electronic device 5200 even when the user and the flight attendant speak different languages. Furthermore, passengers seated next to one another who speak different languages can communicate by using the display portion 5202 of the electronic device 5200. In addition, the electronic device 5200 can function as a message board, displaying a message in English such as "please do not disturb" on the display portion 5202 while the user is asleep, for example.

The electronic device 5200 has a plurality of batteries each of which is for a different function, and only the function to be used is turned on while the other functions not in use are in an off state, whereby power consumption can be reduced. Furthermore, among the plurality of batteries, batteries corresponding to the functions not in operation can be wirelessly charged from the antenna installation portion 5203.

It is difficult to carry a dangerous object on an airplane. The electronic device 5200 having a plurality of small-sized batteries is highly safe, and even if one of the batteries explodes, the damage can be minimized. In addition, even if one battery becomes unavailable because of failure, explosion, or breakage, some of the functions of the electronic device 5200 can still be used by utilizing the other batteries.

The plurality of batteries of the electronic device 5200 provided over the plurality of seats may be designed such that they can be used in emergency when an airplane has an electrical problem. Since all the electronic devices 5200, each of which is provided for each of the plurality of seats, are the same products having the same design, a system may be constructed such that the electronic devices 5200 can be connected in series as an emergency power supply.

As the plurality of small-sized batteries of the electronic device 5200, one or more kinds selected from the following can be used: a lithium ion secondary battery such as a lithium polymer battery, a lithium ion capacitor, an electric double layer capacitor, and a redox capacitor.

The structure described in this embodiment can be used in appropriate combination with the structure described in any of the other embodiments.

Embodiment 5

In this embodiment, an example of an artificial organ that is one embodiment of the present invention will be described.

Figure 14:
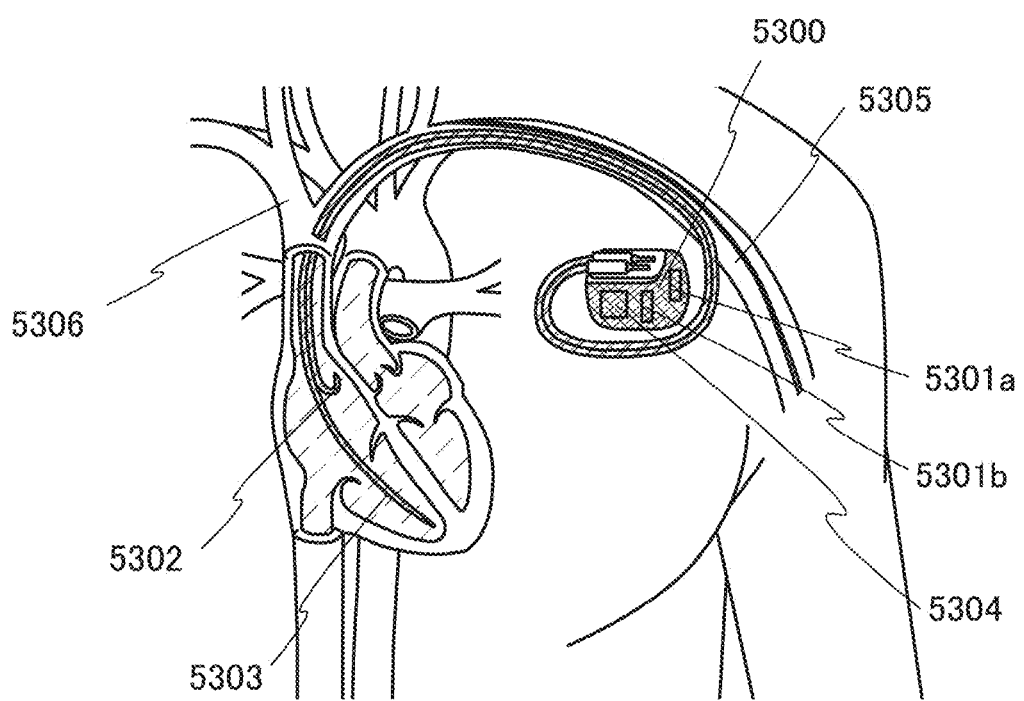
FIG. 14 illustrates an electronic device according to one embodiment of the present invention.

FIG. 14 is a cross-sectional schematic view of an example of a pacemaker.

A pacemaker body 5300 includes at least batteries 5301a and 5301b, a regulator, a control circuit, an antenna 5304, a wire 5302 reaching a right atrium, and a wire 5303 reaching a right ventricle.

The pacemaker body 5300 is implanted in the body by surgery, and the two wires pass through a subclavian vein 5305 and a superior vena cava 5306 of the human body, with the end of one of them placed in the right ventricle and the end of the other of them placed in the right atrium.

The antenna 5304 can receive electric power, and the plurality of batteries 5301a and 5301b are charged with the electric power, which can reduce the frequency of replacing the pacemaker. Since the pacemaker body 5300 has a plurality of batteries, the safety is high, and even when one of the batteries fails, the other can function. In this manner, the plurality of batteries function as auxiliary power supplies. Furthermore, if the battery to be provided in the pacemaker is further divided into a plurality of thin batteries to be mounted on a printed board where control circuits including a CPU and the like are provided, the pacemaker body 5300 can be smaller in size and thickness.

In addition to the antenna 5304 that can receive electric power, an antenna that can transmit a physiological signal may be provided for the pacemaker. For example, a system that monitors the cardiac activity, capable of monitoring physiological signals such as pulses, respiratory rate, heart rate, and body temperature with an external monitoring device may be constructed.

If the pacemaker can be small in size and thickness according to this embodiment, a protrusion generated in the portion where the pacemaker body 5300 is implanted can be unnoticeably small.

Note that how the pacemaker is placed here is just an example, and it can be changed in various ways depending on the heart disease.

Furthermore, this embodiment is not limited to the pacemaker. An artificial ear is an artificial organ that is more widely used than the pacemaker. An artificial ear converts a sound into an electric signal and directly stimulates the auditory nerve with a stimulus device in the cochlea.

An artificial ear includes a first device implanted deep in the ear by surgery and a second device that picks up sounds with a microphone and sends them to the implanted first device. The first device and the second device are not electrically connected to each other, and transmission and reception between the two are conducted wirelessly. The first device includes at least an antenna that receives an electric signal converted from a sound and a wire that reaches the cochlea. The second device includes at least a sound processing portion for converting a sound into an electric signal and a transmitting circuit that transmits the electric signal to the first device.

In this embodiment, a small-sized battery is provided in each of the first device and the second device, whereby the artificial ear can be reduced in size.

Since artificial ears are often implanted by surgery in childhood, reduction in size is desired.

If reduction in size of an artificial ear is achieved by this embodiment, a protrusion generated in the portion where the artificial ear is implanted can be unnoticeably small.

The structure described in this embodiment can be used in appropriate combination with the structure described in any of the other embodiments.

Embodiment 6

In this embodiment, an example of a wearable electronic device that is one embodiment of the present invention will be described.

Figure 15A:
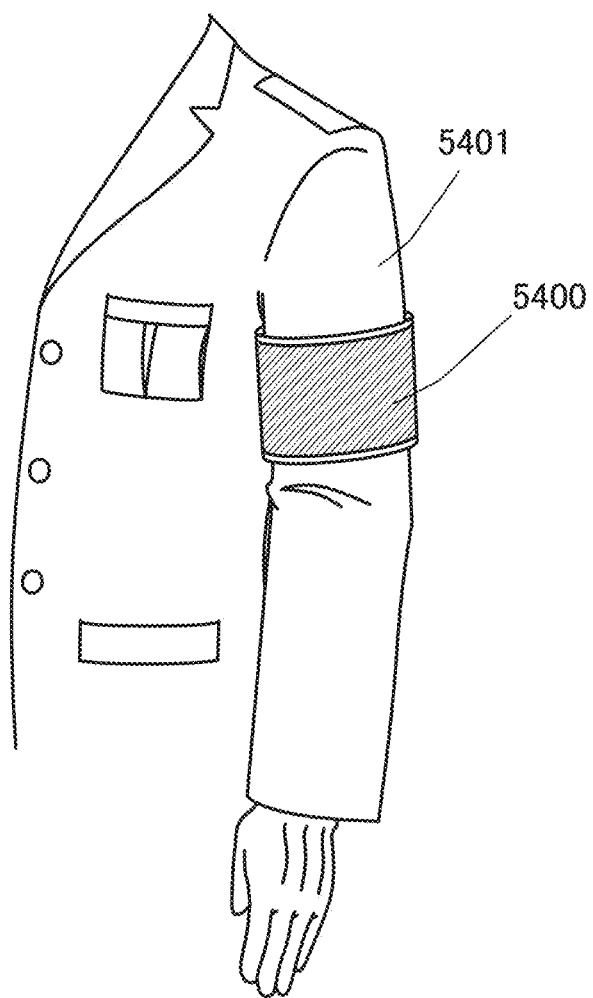
FIGS. 15A and 15B each illustrate an electronic device according to one embodiment of the present invention.

In the case where an electronic device with a complex shape is manufactured, a plurality of small-sized batteries are placed in predetermined places as appropriate, whereby the degree of freedom in design of the electronic device can be increased. As shown in FIG. 15A, an electronic device 5400 has a cylindrical form. In order for the electronic device 5400 to be worn on the human body, a plurality of batteries rather than a single battery are appropriately placed, whereby a feeling of the weight can be reduced. Furthermore, if the device has a number of functions, consumption of a battery in a standby state increases; therefore, batteries for the respective functions are prepared. In the case where the electronic device 5400 having a plurality of batteries has a variety of functions, only the function to be used is turned on and electric power is supplied from the battery corresponding to the function, whereby power consumption can be reduced.

The electronic device 5400 is worn on the left upper arm, over a clothes 5401, as shown in FIG. 15A. Examples of the clothes 5401 include clothes with sleeves, such as a military uniform, an assault jacket, a suit jacket, a uniform, and space suits. There is no particular limitation on how to wear the electronic device 5400, and examples of ways to wear it include sewing it on a portion of clothes that overlaps with the upper arm, attaching it with a Velcro fastener (registered trademark) or the like provided on a portion of clothes that overlaps with the upper arm, fixing it with a band, a clasp, or the like, and binding a band-like leaf spring around an upper arm.

Figure 15B:
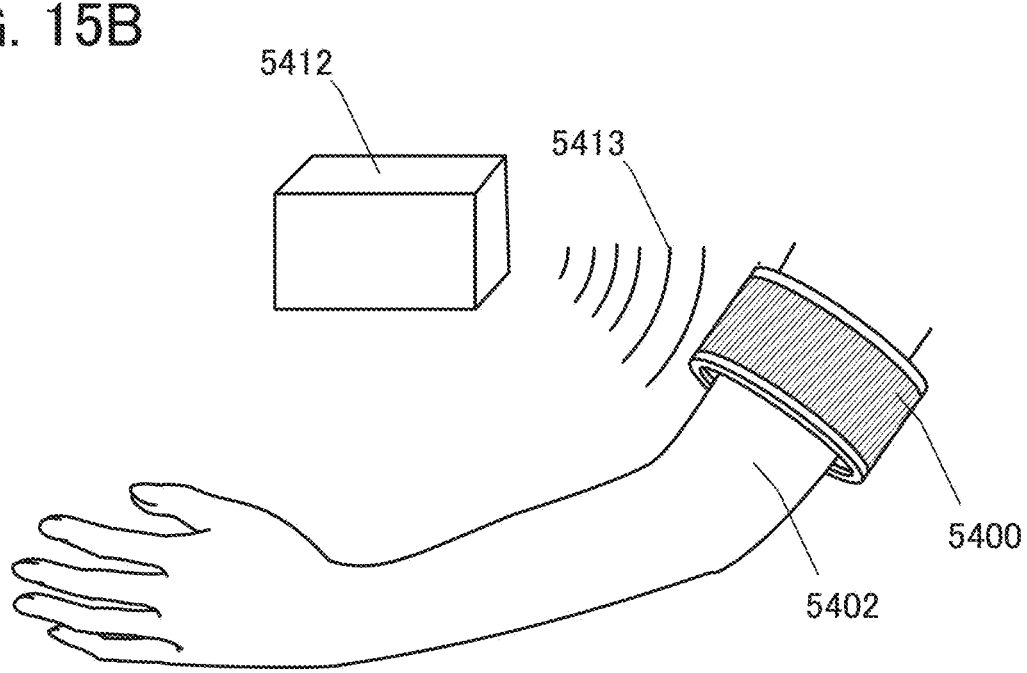

The electronic device 5400 has an antenna. A perspective view in which the electronic device 5400 is worn on the skin and wirelessly charged is shown in FIG. 15B. In FIG. 15B, the electronic device 5400 is worn on an upper arm 5402. A surface of the electronic device 5400 that is to be in contact with the skin is preferably formed using a skin-friendly film or a natural material such as leather, paper, and fabric. The numeral 5412 indicates an electric power transmission device that can wirelessly charge the electronic device 5400 with the use of a radio wave 5413. When provided with an antenna or a circuit that can transmit and receive other data, the electronic device 5400 can transmit and receive other data as well as power. For example, the electronic device 5400 can also be used like a smartphone.

The structure described in this embodiment can be used in appropriate combination with the structure described in any of the other embodiments.

EXPLANATION OF REFERENCE

10: device, 11: CPU, 12: battery, 13: regulator, 14: wireless receiving portion, 15: control module, 16: display portion, 17: battery, 18: regulator, 19: display driver circuit, 20: wireless receiving portion, 21: display module, 22: communication circuit, 23: battery, 24: regulator, 25: wireless receiving portion, 26: communication module, 100: battery, 101: insulating film, 102: positive electrode current collector layer, 103: positive electrode active material layer, 104: solid electrolyte layer, 105: negative electrode active material layer, 106: negative electrode current collector layer, 107: insulating film, 108: wiring, 110: insulating film, 120: battery, 130: battery, 140: battery, 600: transistor, 640: substrate, 652: insulating film, 653: gate insulating film, 654: insulating film, 655: insulating film, 660: oxide semiconductor, 661: oxide semiconductor, 662: oxide semiconductor, 663: oxide semiconductor, 671: source electrode, 672: drain electrode, 673: gate electrode, 674: conductive film, 700: substrate, 701: plug, 702: wiring, 703: plug, 704: plug, 705: wiring, 707: wiring, 720: transistor, 721: impurity region, 722: impurity region, 723: channel region, 724: gate insulating film, 725: sidewall insulating layer, 726: gate electrode: 727: element isolation layer, 730: transistor, 731: insulating film, 732: insulating film, 740: battery, 741: insulating film, 742: insulating film, 750: transistor, 751: impurity region, 752: impurity region, 753: channel region, 754: gate insulating film, 755: sidewall insulating layer, 756: gate electrode, 757: insulating film, 1000: semiconductor device, 1100: semiconductor device, 1200: semiconductor device, 5000: housing, 5001: display portion, 5002: display portion, 5003: speaker, 5004: LED lamp, 5005: operation key, 5006: connection terminal, 5007: sensor, 5008: microphone, 5009: switch, 5010: infrared port, 5011: memory medium reading portion, 5012: support, 5013: earphone, 5014: antenna, 5015: shutter button, 5016: receiving portion, 5100: electronic device, 5101: display portion, 5102: display portion, 5103: steering wheel, 5200: electronic device, 5201: seat, 5202: display portion, 5203: antenna installation portion, 5300: pacemaker body, 5301a: battery, 5301b: battery, 5302: wire, 5303: wire, 5304: antenna, 5305: subclavian vein, 5400: electronic device, 5401: clothes, 5402: upper arm, 5413: radio wave This application is based on Japanese Patent Application serial no. 2014-026312 filed with Japan Patent Office on Feb. 14, 2014, the entire contents of which are hereby incorporated by reference.

What is claimed is:

1. An electronic device comprising:
   a control module, the control module comprising:
      a first circuit;
      a first secondary battery; and
      a first regulator configured to prevent an overcharge of the first secondary battery when the first secondary battery is charged, and
   a communication module, the communication module comprising:
      a second circuit;
      a second secondary battery; and
      a second regulator configured to prevent an overcharge of the second secondary battery when the second secondary battery is charged,
   wherein the first secondary battery is provided over the first circuit,
   wherein the first secondary battery is configured to supply power to the first circuit,
   wherein the second secondary battery is configured to supply power to the second circuit, and
   wherein an off state or an on state of the communication module is controlled by the control module.

2. The electronic device according to claim 1, wherein the first and second secondary batteries are configured to be wirelessly charged via the first and second regulators, respectively.

3. The electronic device according to claim 1, wherein the first secondary battery and the first circuit are provided over a same substrate.

4. The electronic device according to claim 1,
   wherein the first secondary battery and the first circuit are provided over a same substrate, and
   wherein the first secondary battery overlaps with the first circuit.

5. The electronic device according to claim 4, wherein a first transistor is provided under a second transistor.

6. The electronic device according to claim 5,
   wherein the first transistor comprises a first channel formation region comprising silicon, and
   wherein the second transistor comprises a second channel formation region comprising an oxide semiconductor.

7. The electronic device according to claim 6,
   wherein the first secondary battery comprises a solid electrolyte, and
   wherein the first secondary battery is provided on the first circuit.

\* \* \* \* \*